United States Patent
Mellors et al.

(10) Patent No.: US 10,393,698 B2
(45) Date of Patent: *Aug. 27, 2019

(54) PRESSURE DRIVEN MICROFLUIDIC INJECTION FOR CHEMICAL SEPARATIONS

(71) Applicant: The University of North Carolina at Chapel Hill, Chapel Hill, NC (US)

(72) Inventors: John Scott Mellors, Carrboro, NC (US); Erin Anne Redman, Carrboro, NC (US); John Michael Ramsey, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 261 days.

This patent is subject to a terminal disclaimer.

(21) Appl. No.: 15/439,199

(22) Filed: Feb. 22, 2017

(65) Prior Publication Data
US 2017/0322180 A1    Nov. 9, 2017

Related U.S. Application Data

(63) Continuation of application No. 14/987,326, filed on Jan. 4, 2016, now Pat. No. 9,606,082, which is a (Continued)

(51) Int. Cl.
*G01N 27/447* (2006.01)
*G01N 30/16* (2006.01)
(Continued)

(52) U.S. Cl.
CPC .... *G01N 27/44743* (2013.01); *B01L 3/50273* (2013.01); *G01N 27/4473* (2013.01);
(Continued)

(58) Field of Classification Search
CPC .. G01N 27/44743; G01N 30/16; G01N 30/24; G01N 2030/167
See application file for complete search history.

(56) References Cited

U.S. PATENT DOCUMENTS

| | | |
|---|---|---|
| 5,872,010 A | 2/1999 | Karger et al. |
| 5,958,203 A | 9/1999 | Parce et al. |

(Continued)

FOREIGN PATENT DOCUMENTS

| | | |
|---|---|---|
| EP | 2 184 602 A1 | 5/2010 |
| JP | 2000-310613 | 11/2000 |

(Continued)

OTHER PUBLICATIONS

Batz et al. "Chemical Vapor Deposition of Aminopropyl Silanes in Mircrofluidic Channels for Highly Efficient Microchip Capillary Electrophoresis Electrospray Ionization-Mass Spectrometry" *Anal. Chem* 86:3493-3500 (2014).

(Continued)

*Primary Examiner* — Alexander S Noguerola
(74) *Attorney, Agent, or Firm* — Myers Bigel, P.A.

(57) ABSTRACT

Methods that allow independently applied pressures to a BGE reservoir and a sample reservoir for pressure-driven injection that can inject a discrete sample plug into a separation channel that does not require voltage applied to the sample reservoir and can allow for in-channel focusing methods to be used. The methods are particularly suitable for use with a mass spectrometer.

28 Claims, 13 Drawing Sheets

Related U.S. Application Data continuation of application No. 14/708,906, filed on May 11, 2015, now Pat. No. 9,255,905.

(51) Int. Cl.
*B01L 3/00* (2006.01)
*H01J 49/16* (2006.01)
*G01N 30/72* (2006.01)
*B05B 5/00* (2006.01)

(52) U.S. Cl.
CPC ....... *G01N 27/44791* (2013.01); *G01N 30/16* (2013.01); *H01J 49/165* (2013.01); *B01L 2300/0864* (2013.01); *B01L 2400/049* (2013.01); *B01L 2400/0418* (2013.01); *B01L 2400/0421* (2013.01); *B01L 2400/0487* (2013.01); *B01L 2400/0622* (2013.01); *B01L 2400/0666* (2013.01); *B05B 5/00* (2013.01); *G01N 30/7266* (2013.01); *G01N 2030/167* (2013.01)

(56) References Cited

U.S. PATENT DOCUMENTS

| | | |
|---|---|---|
| 6,074,827 A | 6/2000 | Nelson |
| 6,268,220 B1 | 7/2001 | Heinecke |
| 6,375,817 B1 | 4/2002 | Taylor et al. |
| 6,475,363 B1 | 11/2002 | Ramsey |
| 6,833,068 B2 | 12/2004 | Paul et al. |
| 7,391,020 B2 | 6/2008 | Bousse et al. |
| 7,494,577 B2 | 2/2009 | Williams et al. |
| 7,749,365 B2 | 7/2010 | Nguyen et al. |
| 7,846,314 B2 | 12/2010 | Gassmann |
| 7,927,476 B2 | 4/2011 | Tian et al. |
| 9,006,648 B2 | 4/2015 | Ramsey et al. |
| 9,139,426 B2 | 9/2015 | Ramsey et al. |
| 9,255,905 B1 | 2/2016 | Mellors et al. |
| 2001/0005489 A1 | 6/2001 | Roach et al. |
| 2001/0035351 A1 | 11/2001 | Simpson et al. |
| 2002/0112959 A1 | 8/2002 | Xue et al. |
| 2002/0115293 A1 | 8/2002 | Ghodsian |
| 2002/0189946 A1 | 12/2002 | Wainright et al. |
| 2004/0088762 A1 | 5/2004 | Oriedo |
| 2004/0195099 A1 | 10/2004 | Jacobson et al. |
| 2004/0224425 A1 | 11/2004 | Gjerde et al. |
| 2005/0118599 A1 | 6/2005 | Pawliszyn |
| 2006/0254915 A1 | 11/2006 | Hirokawa et al. |
| 2007/0111329 A1 | 5/2007 | Guzman |
| 2007/0134808 A1 | 6/2007 | Sullivan |
| 2010/0084271 A1 | 4/2010 | Santiago |
| 2011/0133077 A1 | 6/2011 | Henion |
| 2013/0327936 A1 | 12/2013 | Ramsey et al. |
| 2014/0238856 A1 | 8/2014 | Ramsey et al. |
| 2014/0272958 A1 | 9/2014 | Ramsey et al. |
| 2014/0360877 A1 | 12/2014 | Ramsey et al. |
| 2015/0099642 A1 | 4/2015 | Barany |

FOREIGN PATENT DOCUMENTS

| | | |
|---|---|---|
| WO | WO 98/04909 A1 | 2/1998 |
| WO | WO 01/69226 A1 | 9/2001 |
| WO | WO 2012/040098 A2 | 3/2012 |
| WO | WO 2012/125318 A2 | 9/2012 |

OTHER PUBLICATIONS

Chambers et al. "Monolithic Integration of Two-Dimensional Liquid Chromatography-Capillary Electrophoresis and Electrospray Ionization on a Microfluidic Device" *Anal. Chem.* 83:842-849 (2011).

Cho et al. "Bias-free pneumatic sample injection in microchip electrophoresis" *Journal of Chromatography A* 1063:253-256 (2005).

Fenn et al. "Electrospray Ionization for Mass Spectrometry of Large Biomolecules" *Science* 246:64-71 (1989).

International Search Report and the Written Opinion of the International Searching Authority corresponding to International Patent Application No. PCT/US2016/031626 (21 pages) (dated Jul. 28, 2016).

Lazar et al. "Subattomole-Sensitivity Microchip Nanoelectrospray Source with Time-of-Flight Mass Spectrometry Detection" *Anal. Chem.* 71:3627-3631 (1999).

Lazar et al. "Novel microfabricated device for electrokinetically induced pressure flow and electrospray ionization mass spectrometry" *Journal of Chromatography A* 892:195-201 (2000).

Lazar et al. "On-Chip Proteolytic Digestion and Analysis Using 'Wrong-Way-Round' Electrospray Time-of-Flight Mass Spectrometry" *Anal. Chem.* 73:1733-1739 (2001).

Lee et al. "Pressure-Driven Sample Injection with Quantitative Liquid Dispensing for On-Chip Electrophoresis" *Analytical Sciences* 20:483-487 (2004).

Lee et al. "Control-free Air Vent System for Ultra-low Volume Sample Injection on a Microfabricated Device" *Analytical Sciences* 21:465-468 (2005).

Mellors et al. "Fully Integrated Glass Microfluidic Device for Performing High-Efficiency Capillary Electrophoresis and Electrospray Ionization Mass Spectrometry" *Anal. Chem.* 80:6881-6887 (2008).

Mellors et al. "Integrated Microfluidic Device for Automated Single Cell Analysis Using Electrophoretic Separation and Electrospray Ionization Mass Spectrometry" *Anal. Chem.* 82:967-973 (2010).

Mellors et al. "Hybrid Capillary/Microfluidic System for Comprehensive Online liquid Chromatography-Capillary Electrophoresis-Electrospray Ionization-Mass Spectrometry" *Anal. Chem.* 85:4100-4106 (2013).

Ramsey et al. "Generating Electrospray from Microchip Devices Using Electroosmotic Pumping" *Anal. Chem.* 69:1174-1178 (1997).

Redman et al. "Integrated Microfluidic Capillary Electrophoresis-Electrospray Ionization Devices with Online MS Detection for the Separation and Characterization of Intact Monoclonal Antibody Variants" *Anal. Chem.* 87: 2264-2272 (2015).

Xue et al. "Integrated Multichannel Microchip Electrospray Ionization Mass Spectrometry: Analysis of Peptides from On-chip Tryptic Digestion of Melittin" *Rapid Communications in Mass Spectrometry* 2:1253-1256 (1997).

Xue et al. "Multichannel Microchip Electrospray Mass Spectrometry" *Anal. Chem.* 69:426-430 (1997).

Zhang et al. "Microfabricated Devices for Capillary Electrophoresis-Electrospray Mass Spectrometry" *Anal. Chem.* 71(15):3258-3264 (1999).

Annesley "Ion Suppression in Mass Spectrometry" *Clinical Chemistry* 49(7):1041-1044 (2003).

Apffel et al. "Enhanced sensitivity for peptide mapping with electrospray liquid chromatography-mass spectrometry in the presence of signal suppression due to trifluoroacetic acid-containing mobile phases" *Journal of Chromatography A* 712:177-190 (1995).

Au et al. "3D-printed microfluidic automation" *Lab Chip* 15:1934-1941 (2015).

Black et al. "Utilizing Microchip Capillary Electrophoresis Electrospray Ionization for Hydrogen Exchange Mass Spectrometry" *Analytical Chemistry* 87:6280-6287 (2015).

Breadmore et al. "Recent advances in enhancing the sensitivity of electrophoresis and electrochromatography in capillaries and microchips (2010-2012)" *Electrophoresis* 34:29-54 (2013)

Breadmore et al. "Recent advances in enhancing the sensitivity of electrophoresis and electrochromatography in capillaries and microchips (2008-2010)" *Electrophoresis* 32:127-148 (2011).

Broyles et al. "Sample Filtration, Concentration, and Separation Integrated on Microfluidic Devices" *Analytical Chemistry* 75(11):2761-2767 (2003).

Busnel et al. "High Capacity Capillary Electrophoresis-Electrospray Ionization Mass Spectrometry: Coupling a Porous Sheathless Interface with Transient-Isotachophoresis" *Analytical Chemistry* 82(22):9476-9483 (2010).

(56) References Cited

OTHER PUBLICATIONS

Dahlin et al. "Poly(dimethylsiloxane)-Based Microchip for Two-Dimensional Solid-Phase Extraction-Capillary Electrophoresis with an Integrated Electrospray Emitter Tip" *Analytical Chemistry* 77(16):5356-5363 (2005).
Dennis et al. "Development of a Photothermal Absorbance Detector for Use with Microfluidic Devices" *Analytical Chemistry* 82(10):4063-4071 (2010).
De Oliveira et al. "20 Years of Fatty Acid Analysis by Capillary Electrophoresis" *Molecules* 19:14094-14113 (2014).
Ermakov et al. "Computer Simulations of Electrokinetic Injection Techniques in Microfluidic Devices" *Analytical Chemistry* 72(15):3512-3517 (2000).
Foote et al. "Preconcentration of Proteins on Microfluidic Devices Using Porous Silica Membranes" *Analytical Chemistry* 77(1):57-63 (2005).
Gilar et al. "Mixed-mode chromatography for fractionation of peptides, phosphopeptides, and sialylated glycopeptides" *Journal of Chromatography A* 1191:162-170 (2008).
Gong et al. "Sudy of injection bias in a simple hydrodynamic injection in microchip CE" *Electrophoresis* 28:1564-1571 (2007).
Guetschow et al. "Subsecond Electrophoretic Separations from Droplet Samples for Screening of Enzyme Modulators" *Analytical Chemistry* 86:10373-10379 (2014).
Hernandez et al. "Analysis of Opiod Peptides by On-Line SPE-CE-ESI-MS" *Electrophoresis* 28:3957-3965 (2007).
Hua et al. "On-chip solid phase extraction and enzyme digestion using cationic PolyE-323 Coatings and porous polymer monoliths coupled to electrospray mass spectrometry" *Journal of Chromatography A* 1218:4039-4044 (2011).
Ibanez et al. "Metabolomics, peptidomics and proteomics applications of capillary electrophoresis-mass spectrometry in Foodomics: A review" *Analytica Chimica Acta* 802:1-13 (2013).
Jacobson et al. "Microchip Capillary Electrophoresis with an Integrated Postcolumn Reactor" *Analytical Chemistry* 66(20):3472-3476 (1994).
Jemere et al. "An integrated solid-phase extraction system for sub-picomolar detection" *Electrophoresis* 23:3537-3544 (2002).
Jorgenson et al. "Free-Zone Electrophoresis in Glass Capillaries" *Clinical Chemistry* 27(9):1551-1553 (1981).
Kang et al. "Polymer monolith-integrated multilayer poly(dimethylsiloxane) microchip for online microextraction and capillary electrophoresis" *Electrophoresis* 31:3028-3034 (2010).
Kašička et al. "Isotachophoretic Electrodesorption of Proteins From an Affinity Adsorbent on a Microscale" *Journal of Chromatography* 273:117-128 (1983).
Kitagawa et al. "Recent applications of on-line sample preconcentration techniques in capillary electrophoresis" *Journal of Chromatography A* 1335:43-60 (2014).
Li et al. "Separation and Identification of Peptides from Gel-Isolated Membrane Proteins Using a Microfabricated Device for Combined Capillary Electrophorsis/Nanoelectrospray Mass Spectrometry" *Analytical Chemistry* 72(3):599-609 (2000).
Li et al. "A novel mixed-mode solid phase extraction coupled with LC-MS/MS for the re-evaluation of free 3-nitrotyrosine in human plasma as an oxidative stress biomarker" *Talanta* 140:45-51 (2015).
Long et al. "Integrated multilayer microfluidic device with a nanoporous membrane interconnect for online coupling of solid-phase extraction to microchip electrophoresis" *Lab Chip* 7:1819-1824 (2007).
Mallet et al. "A study of ion suppression effects in electrospray ionization from mobile phase additives and solid-phase extracts" *Rapid Communications in Mass Spectrometry* 18:49-58 (2004).
Marchiarullo et al. "Towards an integrated microfluidic device for spaceflight clinical diagnostics Microchip-based solid-phase extraction of hydroxyl radical markers" *Journal of Chromatography A* 1200:198-203 (2008).
Medina-Casanellas et al. "Transient isotachophoresis in on-line solid phase extraction capillary electrophoresis time-of-flight-mass spectrometry for peptide analysis in human plasma" *Electrophoresis* 32:1750-1759 (2011).

Nge et al. "Microfluidic chips with reversed-phase monoliths for solid phase extraction and on-chip labeling" *J. Chromatogr A* 1261:129-135 (2012).
Nge et al. "Integrated Affinity and Electrophoresis Systems for Multiplexed Biomarker Analysis, Clinical Applications of Capillary Electrophoresis Methods and Protocols" *Methods in Molecular Biology* 919:189-201 (2013).
Nge et al. "Ion-permeable membrane for on-chip preconcentration and separation of cancer marker proteins" *Electrophoresis* 32:1133-1140 (2011).
Nie et al. "An automated integrated platform for rapid and sensitive multiplexed protein profiling using human saliva samples" *Lab Chip* 14:1087-1098 (2014).
Nuchtavorn et al. "Recent applications of microchip electrophoresis to biomedical analysis" *Journal of Pharmaceutical and Biomedical Analysis* 113:72-96 (2015).
Oblath et al. "A microfluidic chip integrating DNA extraction and real-time PCR for the detection of bacteria in saliva" *Lab Chip* 13:1325-1332 (2013).
Oleschuk et al. "Trapping of Bead-Based Reagents within Microfluidic Systems: On-Chip Solid-Phase Extraction and Electrochromatography" *Analytical Chemistry* 72:585-590 (2000).
Osbourn et al. "On-line preconcentration methods for capillary electrophoresis" *Electrophoresis* 21:2768-2779 (2000).
Pascali et al. "Recent advances in the application of CE to Forensic sciences, an update over years 2009-2011" *Electrophoresis* 33:117-126 (2012).
Pontillo et al. "CE-MS-based proteomics in biomarker discovery and clinical application" *Proteomics Clin. Appl.* 9:322-334 (2015).
Puig et al. "Sorbent preconcentration procedures coupled to capillary electrophoresis for environmental and biological applications" *Analytica Chimica Acta* 616:1-18 (2008).
Ramautar et al. "Developments in coupled solid-phase extraction-capillary electrophoresis 2009-2011" *Electrophoresis* 33:243-250 (2012).
Ramautar et al. "Developments in coupled solid-phase extraction-capillary electrophoresis 2011-2013" *Electrophoresis* 35:128-137 (2014).
Robledo et al. "Review of the CE-MS platform as a powerful alternative to conventional couplings in bio-omics and target-based applications" *Electrophoresis* 35:2292-2308 (2014).
Rogeberg et al. "On-line solid phase extraction-liquid chromatography, with emphasis on modern bioanalysis and miniaturized systems" *Journal of Pharmaceutical and Biomedical Analysis* 87:120-129 (2014).
Saito et al. "Instrumentation design for hydrodynamic sample injection in microchip electrophoresis: A review" *Electrophoresis* 33:2614-2623 (2012).
Smejkal et al. "Microfluidic isotachophoresis: A review" *Electrophoresis* 34:1493-1509 (2013).
Tempels et al. "On-line coupling of SPE and DE-MS for peptide analysis" *Electrophoresis* 28:1319-1326 (2007).
Timerbaev "Capillary electrophoresis of inorganic ions: An update" *Electrophoresis* 25:4008-4031 (2004).
Tomlinson "Enhanced Performance Membrane Preconcentration-Capillary Electrophoresis-Mass Spectrometry (mPC-DE-MS) in Conjunction with Transient Isotachophoresis for Analysis of Peptide Mixtures" *J. High Resol. Chromatogr.* 18:384-386 (1995).
Wang et al. "Capillary Electrophoresis-Mass Spectrometry in Metabolomics: The Potential for Driving Drug Discovery and Development" *Current Drug Metabolism* 14(7):807-813 (2013).
Wang et al. "Multifunctional protein processing chip with integrated digestion, solid-phase extraction, separation and electrospray" *Electrophoresis* 31:3703-3710 (2010).
Waterval et al. "Qualitative analysis of pharmaceutically active peptides using on-capillary analyte preconcentration transient isotachophoresis" *Electrophoresis* 21:2851-2858 (2000).
Waters "An Overview of the Principles of $MS^E$, The Engine that Drives MS Performance" [White Paper] 8 pages. (2011).
Yang et al. "Membrane Preconcentration CE, A new approach to preconcentrating samples before separation" *Analytical Chemistry News & Features* 71:183A-189A (1999).

PRESSURE DRIVEN MICROFLUIDIC INJECTION FOR CHEMICAL SEPARATIONS

RELATED APPLICATIONS

This application is a continuation application of U.S. patent application Ser. No. 14/987,326, filed Jan. 4, 2016, which is a continuation application of U.S. patent application Ser. No. 14/708,906, filed May 11, 2015, the contents of which are hereby incorporated by reference as if recited in full herein.

STATEMENT OF FEDERAL SUPPORT

This invention was made with government support under Grant No. GM066018 awarded by the National Institutes of Health and Grant No. W911NF-12-1-0539 awarded by the United States Army. The United States government has certain rights in the invention.

FIELD OF THE INVENTION

This invention is related to microfluidic sample processing that may be particularly suitable for electrospray ionization and/or sample processing systems that interface with mass spectrometers.

BACKGROUND OF THE INVENTION

Electrospray ionization ("ESI") is an important technique for the analysis of biological materials contained in solution by mass spectrometry. See, e.g., Cole, R. B. *Electrospray Ionization Mass Spectrometry: Fundamentals, Instrumentation & Applications*; John Wiley and Sons, Inc.: New York, 1997. Electrospray ionization was developed in the late 1980s and was popularized by the work of Fenn. See, e.g., Fenn J B, Mann M, Meng C K, Wong S F & Whitehouse C M (1989), *Electrospray ionization for mass-spectrometry of large biomolecules, Science* 246, 64-71. Simplistically, electrospray ionization involves the use of electric fields to disperse a sample solution into charged droplets. Through subsequent evaporation of the droplets, analyte ions contained in the droplet are either field emitted from the droplet surface or the ions are desolvated resulting in gas phase analyte ions. The source of the liquid exposed to the electric field and to be dispersed is ideally one of small areal extent as the size of the electrospray emitter directly influences the size of droplets produced. Smaller droplets desolvate more rapidly and have fewer molecules present per droplet leading to greater ionization efficiencies. These ions can be characterized by a mass analyzer to determine the mass-to-charge ratio. Further analyte structural information can be obtained by employing tandem mass spectrometry techniques.

Separation of analytes prior to electrospray ionization is important for minimizing ionization suppression and MS spectral complexity. Microfluidic capillary electrophoresis with integrated electrospray ionization has been demonstrated as a fast and efficient method of coupling a liquid phase chemical separation with mass spectroscopy detection. See, e.g., Anal. Chem. 2008, 50, 6881-6887; and Anal. Chem. 2015, 87, 2264-2272. Conventional microfluidic methods that employ electrokinetic flow of sample into the separation channel are subject to injection bias and cannot effectively be used for some on-device sample focusing methods. Further, the injection of a well-defined band of sample into the separation channel of the microfluidic device can be important to achieving an efficient separation.

SUMMARY OF EMBODIMENTS OF THE INVENTION

Embodiments of the invention provide simple, pressure-driven injection methods that can independently be applied to a plurality of different fluid reservoirs. Precise volumes of sample can be delivered into the separation without injection bias.

In some embodiments, the pressure-driven injection methods can also be used with on-device sample focusing methods such as transient isotachophoresis.

The pressure-driven injection method has advantages over other microfluidic injection methods in that it can use a simple channel geometry, but it is capable of generating any desired sample plug size by simply adjusting the injection time and/or pressure. These methods are free of electrokinetic injection bias and no voltage is required to be applied to the sample reservoir. The methods are suitable for performing online sample concentration methods such as transient isotachophoresis (tITP), because sample plugs with significantly different properties (electrical conductivity, pH, and/or viscosity) compared to the background electrolyte can be injected to equal extents.

Embodiments of the invention are directed to methods of sample processing. The methods include: (a) providing a microfluidic device with at least one separation channel in fluid communication with a background electrolyte (BGE) reservoir and a sample reservoir having a sample channel that merges into the separation channel; (b) injecting a fluid sample from the sample reservoir into the separation channel downstream of the BGE reservoir by concurrently applying a defined pressure to the BGE reservoir and a defined pressure to the sample reservoir; (c) then clearing a trailing end of the sample from the sample channel and flowing fluid from the BGE reservoir to deliver a plug of the sample in the separation channel in response to reducing or removing the pressure applied to the sample reservoir while applying pressure to the BGE reservoir so that pressure applied to the BGE reservoir is greater than pressure then applied to the sample reservoir; and then (d) electrophoretically separating the delivered sample in the separation channel by applying voltage to the BGE reservoir and a downstream location of the separation channel.

The injecting, clearing and electrophoretic separation can be carried out without applying a voltage to the sample reservoir.

The electrophoretic separation can be carried out by further reducing or removing pressure applied to the BGE reservoir while applying the voltage.

The method can also include electronically adjusting a duration of the pressure or increasing or decreasing the pressure applied to the sample reservoir and/or BGE reservoir for the injecting and/or clearing to adjust a size of the plug of the sample delivered to the separation channel.

The eletrophoretic separation can be carried out by removing pressure applied to the BGE reservoir while applying the voltage to the BGE reservoir.

The method can include electronically adjusting a duration of the pressure applied to the sample reservoir and/or BGE reservoir for the injecting step.

The method can include controlling a duration and magnitude of the pressure applied to the BGE reservoir to adjust a size of the plug of the sample delivered to the separation channel.

The clearing the trailing end of the sample to deliver the plug of the sample into the separation channel can be carried out by removing the pressure applied to the sample reservoir while applying the pressure to the BGE reservoir.

The method can include discharging the electrophoretically separated sample from the microfluidic device via at least one emitter on the microfluidic device toward at least one of a collection device for subsequent analysis or an entrance of a mass spectrometer.

The method can further include electrospray emitting the electrophoretically separated sample from the microfluidic device via at least one ESI emitter on the microfluidic device to spray toward a collection device for subsequent analysis and/or toward an entrance of a mass spectrometer.

The microfluidic device can include at least one electroosmotic (EO) pump onboard the microfluidic device for driving the discharging (e.g., electrospray emitting).

The pressures applied to the BGE reservoir and the sample reservoir during the injecting step can be between 0.1 and 30 psi.

The pressure applied to the sample reservoir during the injecting step can be between 1 and 10 psi. The reducing or removing the pressure applied to the sample reservoir during the clearing step can be carried out by venting the pressurized gas in the sample reservoir headspace gas (typically to atmosphere, but other venting arrangements may be used).

The pressure applied to the BGE reservoir and the pressure applied to the sample reservoir during the injecting step can be between 2 and 10 psi. No pressure can be applied to the sample reservoir during the clearing step and the pressure applied to the BGE reservoir during the clearing step can be between 1-5 psi.

The injecting step can be carried out by applying the defined pressures for between 1 and 30 seconds.

The method can include attaching a first pressure supply tube in communication with a pressurized gas supply and a first valve to the BGE reservoir. The tube can include a voltage input (e.g., electrode) to the BGE reservoir. The method can include attaching a second pressure supply tube in communication with a pressurized gas supply and a second valve to the sample reservoir. The method can include electronically opening and closing the first and second valves to carry out the injecting and eletrophoretic separation.

The BGE reservoir can be in fluid communication with a BGE channel that merges into or connects to an end of the separation channel and the sample reservoir channel can be downstream of the BGE channel and can extend laterally from the sample reservoir to connect to the separation channel (directly or indirectly) across from a laterally extending sample waste channel that connects to a sample waste reservoir.

The microfluidic device can include a sample waste channel that connects to a sample waste reservoir. The sample channel and sample waste channel can define an orthogonal flow path across the separation channel downstream of the BGE reservoir.

The method can include detecting peak signals of analytes and/or bands of the sample using a mass spectrometer and generating electropherograms of the sample.

The electrophoretic separation can be completely free of injection bias so that peak areas in the electropherograms are consistent for later eluting analytes in the delivered sample.

The delivered sample can include an electrolyte that has greater electrophoretic mobility than analyte ions in the sample for transient isotachophoresis.

The sample can include one or more of amino acids, polar metabolites, charged molecules, molecules with electrophoretic mobility, peptides, proteins, and molecules extracted from one or more of biofluids, blood, serum, urine, dried blood, cell growth media, lysed cells, environmental samples, beverages and food.

Yet other embodiments are directed to microfluidic analysis systems. The systems include a microfluidic device comprising at least one separation channel in fluid communication with a background electrolyte (BGE) reservoir, and a sample reservoir having a sample channel that merges into the separation channel and a sample waste channel that merges into the separation channel. The systems also include a first pressure supply tube in communication with a pressurized gas supply and a first valve, the tube having a voltage input attached to the BGE reservoir. The systems also include a second pressure supply tube in communication with a pressurized gas supply and a second valve attached to the sample reservoir. The systems also include a controller in communication with a voltage source (typically for a high voltage input), and the first and second valves (and optionally at least one pressurized gas supply for the first/second supply tubes) configured to direct the first and second valves to open and close to carry out a respective sample injection into the at least one separation channel, then the electrophoretic separation. Sample injection can be carried out using only pressure applied to the BGE reservoir and sample reservoir from the first and second supply tubes without any electrokinetic voltage.

The controller can be configured to have a defined timing sequence for applying pressures between 0.1 and 30 psi to a headspace of the BGE reservoir via the first supply tube and to a headspace of the sample reservoir via the second supply tube for defined durations between 1 and 30 seconds to inject a respective sample into the at least one separation channel.

The controller can be configured to independently apply a defined pressure to the sample reservoir and a defined pressure to the BGE reservoir. The microfluidic device can include at least one EU pump in communication with the separation channel and/or at least one emitter for causing the separated sample to electrospray out of the at least one emitter toward a collection device for subsequent analysis and/or toward an entrance of a mass spectrometer.

The controller can be configured to concurrently supply pressure that is between 0.1 psi and 30 psi to the BGE reservoir and the sample reservoir, then reduce or remove the pressure applied to the sample reservoir while applying pressure to the BGE reservoir so that pressure applied to the BGE reservoir is greater than any pressure then applied to the sample reservoir to clear a trailing end of the sample from the sample channel and flow fluid from the BGE reservoir to thereby deliver a plug of the sample in the separation channel in response. The controller can be configured to then further reduce or removes pressure applied to the BGE reservoir while applying a voltage to the BGE reservoir and a downstream location of the separation channel for the electrophoretic separation, all without applying any voltage to the sample reservoir.

The first and second valves can be three-way valves that can vent pressurized gas in respective first and second supply lines in response to a control signal from the controller.

Yet other embodiments are directed to mass spectrometer analyzer systems. The systems include a mass spectrometer with an entrance and a microfluidic device onboard or in communication with the mass spectrometer. The microfluidic device includes at least one separation channel in fluid communication with a background electrolyte (BGE) reservoir, a sample reservoir having a sample channel that merges into the separation channel and a sample waste channel that merges into the separation channel. The systems further include a first pressure supply tube attached to the BGE reservoir and in communication with a pressurized gas supply and a first valve. The systems also include a voltage input attached to the BGE reservoir and a second pressure supply tube in communication with a pressurized gas supply and a second valve attached to the sample reservoir. The systems also include at least one power source in communication with the BGE reservoir for providing the voltage input and at least one pressure source in fluid communication with the first and second pressure supply tubes. The systems also include at least one controller configured to control the at least one power source for application of an electric field to the microfluidic device and to control pressures supplied to respective headspaces of the sample reservoir and BGE reservoir. Loading of samples into the separation channel can be performed using pressure without any voltage applied to the BGE reservoir and sample reservoir of the microfluidic device.

The first and second valves can be three-way valves that can controllably vent respective headspace pressure.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 12A (the top electropherogram) resulted from an electrokinetically gated injection. FIG. 12B (the bottom electropherogram) resulted from the new pressure driven injection method with a sample loading time of 3 seconds at 2 psi.

FIG. 14A (the top electropherogram) resulted from an electrokinetically gated injection. FIG. 14B (the bottom electropherogram) resulted from the new pressure driven injection method with a sample loading time of 3 seconds at 2 psi.

FIG. 15A (on the left) shows the effect of increased sample loading when the leading electrolyte concentration is too low to support tITP. This sample contained no added salt to the BGE. The electropherograms in FIG. 15B (on the right) show how tITP leads to sharp peaks of increasing concentration when larger amounts of a sample containing a sufficient concentration of leading electrolyte are loaded. This sample contained 100 mM sodium chloride.

FIG. 16A shows a sample injected (for the top electropherogram) contained 100 mM sodium chloride. The sample injected for FIG. 16B (the bottom electropherogram) contained 100 mM ammonium acetate. Both samples were injected for 10 seconds at 2 psi.

DESCRIPTION OF EMBODIMENTS OF THE INVENTION

Figure 1A:
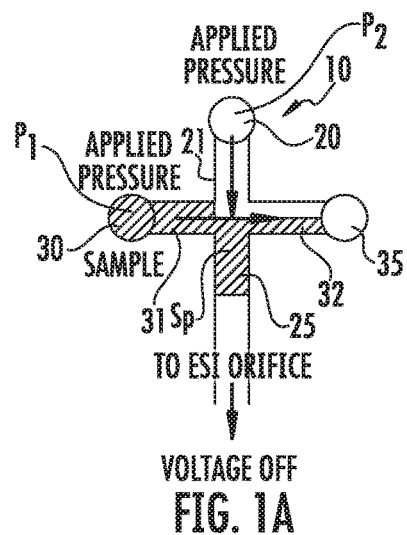
FIGS. 1A-1C are schematic illustrations of a sequence of pressure events of a microfluidic device used to inject sample into a separation channel according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. The abbreviations "FIG. and "FIG.") for the word "Figure" can be used interchangeably in the text and figures.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "about" means that the stated number can vary from that value by +/−20%.

The term "analyte" refers to a molecule or substance undergoing analysis, typically, at least for mass spectrometry analysis, having an ion or ions of interest in a mass-to-charge (m/z) range of interest. The analyte can comprise biomolecules such as polymers, peptides, proteins and the like. Embodiments of the invention are particularly suitable for analyzing intact monoclonal antibodies. Embodiments of the invention are particularly suitable for analyzing metabolites.

The term "microchip" refers to a substantially planar, thin, and, in some embodiments, rigid device. The term "thin" refers to a thickness dimension that is less than about 10 mm, typically about 1 mm or less. The microchip typically has a width and length that is less than about 6 inches and a thickness that is less than about 5 mm, typically between about 2000 µm to about 250 µm.

The terms "integrated" and "integral" and derivatives thereof means that the component or process is incorporated into or carried out by a fluidic device.

The term "high voltage" refers to voltage in the kV range, typically between about 1-100 kV, more typically between about 1-20 kV. ESI processes can employ potentials of a few kVs, typically between about 1 kV to about 5 kV, for example. Although other voltages may be appropriate.

The term "microfluidic" refers to fluid flow channels that have sub-millimeter or smaller size width and/or depth (e.g., the term includes nanometer size channels) and includes channels with width or depth in a size range of about tens to hundreds of microns.

All of the document references (patents, patent applications and articles) are hereby incorporated by reference as if recited in full herein.

In typical free zone capillary electrophoresis (CE) experiments, a sample plug is injected into a column, and an applied electric field causes sample components to separate according to differences in their mobilities. The mobility of a molecule is the sum of its electrophoretic mobility and the electroosmotic mobility, and any pressure driven flow, if present, of the separation column. The term "plug" with respect to "sample" refers to a quantity of a sample collected/localized within a spatial region, such as within a spatial region of a carrier fluid. The plug can be a physical band or segment with defined leading and trailing ends so that there is a distinct clearance between successive plugs or bands.

The analyte in a sample can be any analyte of interest including, for example, various mixtures including synthetic and biological macromolecules, nanoparticles, small molecules, DNA, nucleic acids/polynucleic acids, peptides, proteins and the like. The sample can include one or more polar metabolites such as amino acids or charged molecules, molecules, peptides, and proteins. The sample may also or alternatively include molecules extracted from biofluids, blood, serum, urine, dried blood, cell growth media, lysed cells, beverages or food; or environmental samples such as water or soil.

Figure 2A:
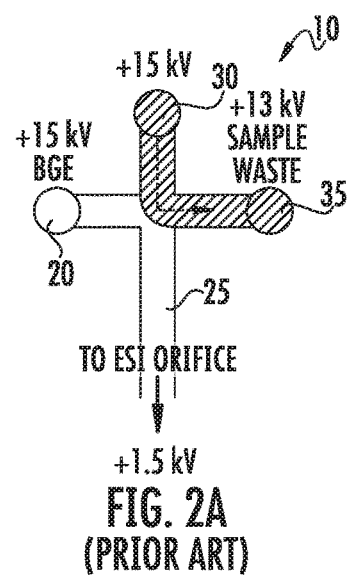
FIGS. 2A-2C are schematic illustrations of the same microfluidic device shown in FIGS. 1A-1C, but illustrating a prior art electrokinetic injection.
Figure 2B:
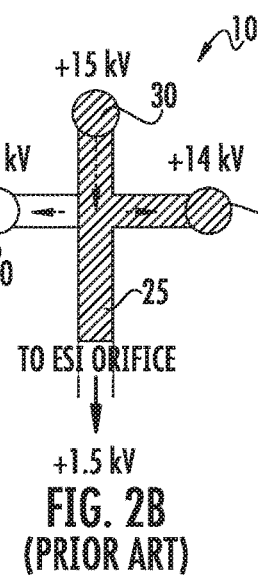
Figure 2C:
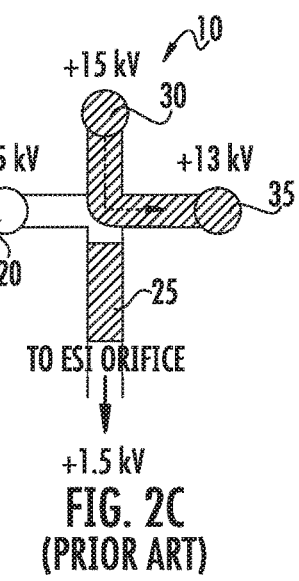

In the past, as shown in FIGS. 2A-2C, electrokinetic (EK) gate methods using a sequence of different voltages applied to the microfluidic device 10 for sample injection.

Generally stated, embodiments of the present invention use pressure to inject samples of a microfluidic device 10 for microchip capillary electrophoresis (CE). The pressure-drive method has advantages over other microfluidic injection methods such as voltage-driven loading methods, in that it can use a simple channel geometry, but is capable of generating desired sample plug Sp sizes by simply adjusting the injection time and/or pressure applied to the reservoirs 20, 30. This method is also typically free of eletrokinetic injection bias and no voltage is required to be applied to the sample reservoir 30.

The pressure-driven methods can be particularly suitable for performing online sample concentration methods such as transient isotachophoresis (tITP), because sample plugs Sp with significantly different properties (electrical conductivity, pH, or viscosity) compared to the background electrolyte can be injected. Salt or other electrolyte material in the sample/sample reservoir 30 can be used for tITP. The pressure-driven operation can position a well-defined band of sample (sample plug Sp) into the separation channel 25 of the microfluidic device using only pressure-driven flow and can also be used for online sample focusing methods that are not possible by other microfluidic injection methods.

Figure 1B:
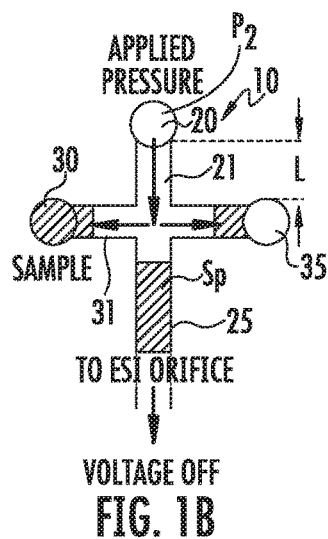
Figure 1C:
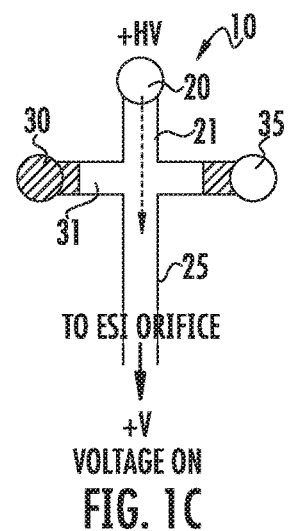

FIGS. 1A and 1B illustrate pressure-driven injection while FIGS. 2A and 2B illustrate voltage driven/gated methods by way of comparison. FIGS. 1C and 2C illustrate respective, subsequent transport/separation in a transport channel 25. FIGS. 1A-1C are shown above FIGS. 2A-2C for ease of discussion and by way of an exemplary embodiment. The noted voltages (and polarity) are also by way of example.

Figure 7A:
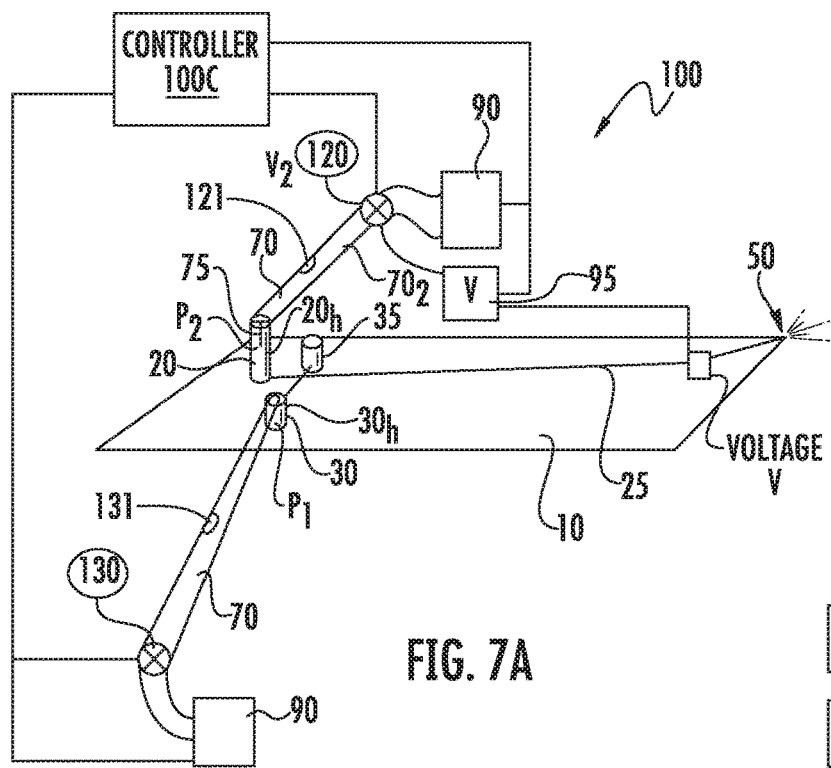
FIG. 7A is a schematic illustration of a microfluidic system according to embodiments of the present invention.
Figure 7B:
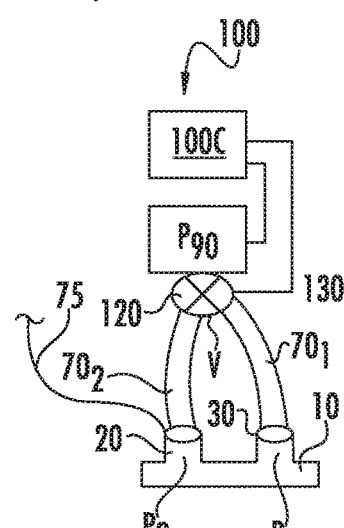
FIG. 7B is a schematic illustration of another embodiment of a microfluidic system according to embodiments of the present invention.

Referring to FIGS. 1A, 1B and 1C, head pressure can be applied to two different fluid reservoirs 20, 30 on or in communication with the microfluidic device 10, typically using off-device (e.g., off-chip) on/off valves 120, 130 (FIGS. 7A, 7B). The term "head pressure" refers to the gas pressure in a sealed headspace of the reservoir above the liquid. The head pressure of the BGE reservoir 20 is labeled P2 and the head pressure of the sample reservoir 30 is labeled P1. A controller 100c (FIGS. 7A, 7B) can be in communication with the valves 120, 130 to independently control when the pressures P1, P2 are applied at the respective reservoirs 20, 30. Thus, for sample loading no voltage is required to be applied to either the BGE reservoir 20 or the sample reservoir 30 (FIGS. 1A, 1B, for example).

The microfluidic channels 25, 31, 32 within the device 10 can, in some embodiments, be configured to form a simple injection cross.

The background electrolyte (BGE) reservoir 20 can reside at a top above the separation channel 25. The BGE reservoir 20 can reside directly adjacent the separation channel or may have a BGE flow channel 21 that merges into the separation channel 25 to position the BGE reservoir 20 a distance away from the sample channel 31 and the sample waste channel 32. Referring to FIG. 1B, the BGE channel 21 can have a length "L" extending from the BGE reservoir 20 to the sample channel 31 and/or the sample channel 31 and waste channel 32 cross/intersection with the separation channel 25. The length "L" can be any suitable length such as between 1-200 mm long. Also, the length of one or more of the channels 21, 31, 32, can be any suitable length such as about 1 mm, about 5 mm, about 10 mm, about 20 mm, about 30 mm, about 40 mm, about 50 mm, about 60 mm, about 70 mm, about 80 mm, about 90 mm, or about 100 mm, in some embodiments, but other lengths can be used. Where used, the injection cross configuration may be such that channels 21, 31 and 32 have substantially the same length or different lengths, but typically lengths that are much less than the length of the separation channel 25. The sample and sample waste channels 31, 32, can be longer or shorter than the BGE channel 21 and may, for example, be between 1-20 mm long. In some embodiments, the sample and sample waste channels 31, 32 are about 8 mm in length.

In the embodiment shown in FIGS. 1A, 1B and 1C, the microfluidic device 10 has cross channels defined by the sample channel 31 and the sample waste channel 32, which can reside on opposing sides of the separation channel 25 and may optionally be orthogonal to and extend across to intersect the separation channel 25. The BGE reservoir 20 can be at the top of the separation channel 25 (directly or via the BGE channel 21). The cross channels 31, 32 may also be offset from each other.

In some embodiments, the sample waste channel 32 may be excluded. Thus, the use of a "tee" intersection of the sample channel 31 (in lieu of the cross channel configuration) to the separation channel 25 may be used and may be implemented using a relatively precise pressure on the BGE reservoir 20 to hold that fluid stationary for injection/sample loading.

Referring to FIG. 1A, pressure is initially concurrently applied to the sample reservoir 30 (P1) and the BGE reservoir 20 (P2) to drive sample from the sample reservoir 30 (shown by the hatched region and the directional arrows) into the separation channel 25 from the sample channel 31, and typically the sample waste channel 32, but not the BGE channel 21. When a plug of a sample Sp in the separation channel 25 reaches a desired length (typically downstream of both the BGE reservoir 20 and the sample reservoir 30), as shown in FIG. 1B, pressure is decreased or released from the sample reservoir 30, but pressure is kept on at the BGE reservoir 20. As shown by the arrows, flow from the BGE channel 21 clears sample in the sample and sample waste channels, leaving a defined plug of sample Sp (trailing end is separated from any adjacent sample in the cross channels 31, 32) in the primary fluid transport (e.g., separation) channel 25. This pressure drive/injection is carried out without requiring any voltage input to the sample reservoir 30. At this point, as shown in FIG. 1C, the pressure is released from the BGE reservoir 20 and voltage is applied between the BGE reservoir 20 and the separation channel 25 at a downstream location, typically an end portion or terminus of the separation channel 25 to perform an electrophoretic separation.

The voltage applied to the BGE reservoir 20 can be a high voltage HV as shown, although lower voltages may be used in some embodiments. The voltage V applied downstream can be a lower voltage than the voltage applied to the BGE reservoir 20. The lower voltage V can be any suitable EK driving voltage and may be between 10%-50% of the BGE reservoir voltage. Voltage can vary and typically ranges from about +1 kV to +30 kV and the lower voltage might range from 0 to +4 kV. But, the voltages and polarity can vary for different applications. For example, the polarity of the separation could be reversed so that the high voltage input shown in FIG. 1C is negative, or closer to zero (0) and the opposing voltage (shown in FIG. 1C as the "low voltage" input) could be higher or even negative depending on the relative length of the microfluidic channels, the charge of the analytes, and the polarity of the ESI process.

The pressures applied to the headspaces of the reservoirs 20, 30 can be low pressures, typically between 0.1 psi and 30 psi, more typically between 0.5 and 10 psi, such as about 0.5 psi, about 1 psi, about 1.5 psi, about 2 psi, about 2.5 psi, about 3 psi, about 3.5 psi, about 4 psi, about 4.5 psi, about 5 psi, about 5.5 psi, about 6 psi, about 6.5 psi, about 7 psi, about 8 psi, about 8.5 psi, about 9 psi, about 9.5 psi and about 10 psi.

The pressures can be supplied by respective gas supply lines 70 sealably attached to respective reservoirs 20, 30, typically conduits or lengths of tubing from at least one pressurized gas source 90 (FIGS. 7A, 7B, 9A, 9B). The pressurized gas for providing the pressure-drive can comprise air, noble gases such as helium or nitrogen or other inert gases. FIG. 7A illustrates discrete valves 120,130 for the gas supply lines $70_2$, $70_1$, respectively. Either or both of valves 120, 130 can be three-way valves.

In some embodiments, the pressure applied concurrently to the BGE reservoir 20 and the sample reservoir 30 for the injection (FIG. 1A) is between 1 and 5 psi for between 1-5 seconds. Then, for the clearing of the tail end of the sample (FIG. 1B), the pressure in the BGE reservoir 20 can be held the same or reduced by 10-80% and the pressure in the sample reservoir 30 can be reduced more than the reduction in the pressure of the BGE reservoir 20, e.g., typically so that it is less than 0.1 psi, e.g., zero or at ambient or atmospheric pressure or below ambient or atmospheric pressure (e.g., under vacuum).

The clearing pressure on the BGE reservoir 20 can be held for a time that is less than the injection time where pressure is applied to both reservoirs 20, 30. The clearing pressure time for the pressure applied only to the BGE reservoir 20 can be 2 seconds or less, 1 second or less or 0.5 seconds, for example.

As noted above, tITP has been previously described as an online sample focusing method for capillary electrophoresis. This phenomenon works when the sample contains a relatively large concentration of an electrolyte (termed the leading electrolyte) that has higher electrophoretic mobility than the analyte ions. As is well known, the leading electrolyte is typically added to the sample solution. The leading electrolyte concentration should be significantly greater (such as at least 5× or 10× greater) than the electrolyte concentration in the background electrolyte to provide a sufficient minimum conductivity difference between the background electrolyte and the leading electrolyte. This is the situation that exists for the pressure-driven injection of samples with high concentration of sodium chloride or other defined electrolyte. For example, for a pH 2.2 background electrolyte with a hydronium concentration of approximately 6 mM, a 15 mM leading electrolyte is too low, but concentrations at or above 50 mM are sufficient for tITP to be observed.

To take advantage of the sample focusing effects of tITP one can inject a larger band of this sample relative to other sample processing/analysis methods and may use a suitable sample formulation with the large concentration of the electrolyte. This new pressure-driven injection method allows increased if not total or complete freedom in altering the size of the sample band, simply by changing the head pressure and/or the duration of the applied pressure for the sample loading step. The BGE reservoir 20 can include liquid electrolyte comprising sodium or salt in sufficient amount for tITP.

Figure 3:
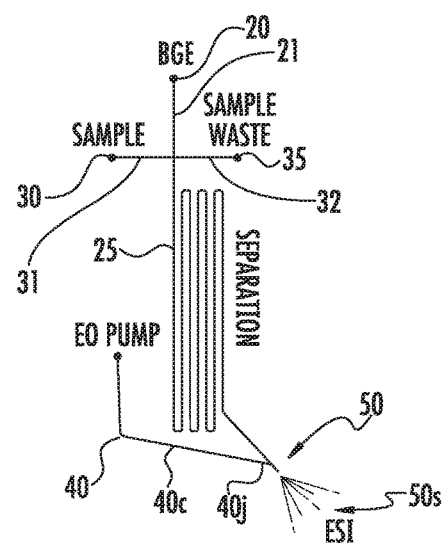
FIG. 3 is a schematic illustration of an exemplary microfluidic device that can be used with pressure-driven injection according to some embodiments of the present invention.
Figure 9A:
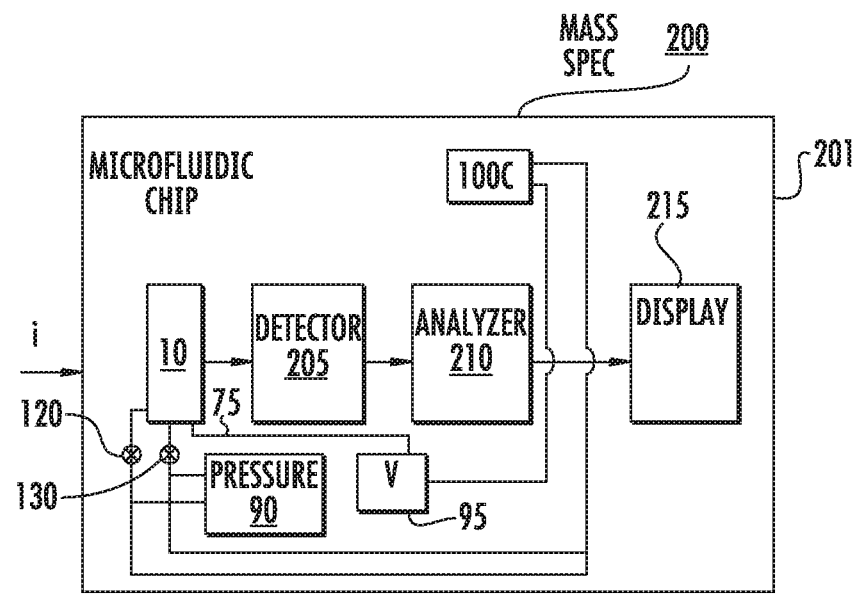
FIG. 9A is a schematic illustration of a portable MS device with an onboard microfluidic system that has pressure-driven injection according to embodiments of the present invention.
Figure 9B:
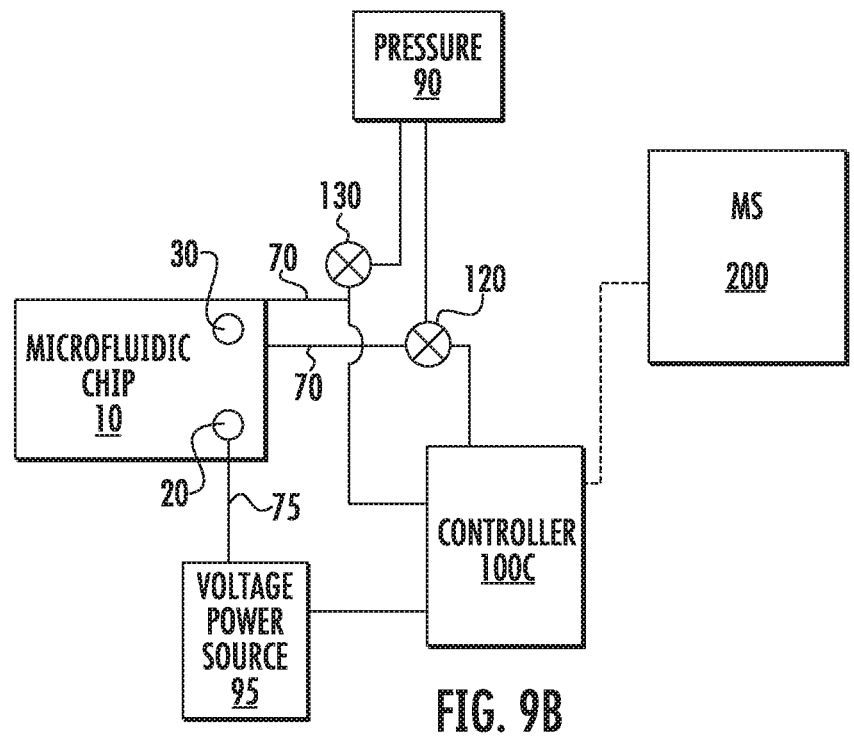
FIG. 9B is a schematic illustration of an external MS in communication with a microfluidic device according to embodiments of the present invention.

FIG. 3 illustrates that the microfluidic device 10 can include an electroosmotic (EO) pump 40 and at least one electrospray ionization (ESI) emitter 50 that can spray a separated sample 50s for analysis. The electrospray from the at least one emitter 50 can be provided to a collection device for subsequent analysis and/or toward a detector of a mass spectrometer 200 (FIG. 9A, 9B).

The separation channel 25 is shown in FIG. 3 as having a serpentine shape but other configurations may be used. For example, the geometry of the separation channel 25 can be straight or curved, and the cross-sectional profiles of the channels do not all have to be the same. For further discussion of exemplary microfluidic devices, see, e.g., U.S. patent application Ser. Nos. 14/001,549 and 14/368,971, the contents of which are hereby incorporated by reference herein.

One or both of the reservoirs 20, 30 can be in fluid communication with an external fluid source to provide fluid thereto during analysis and/or one or both of the reservoirs 20, 30 may be pre-loaded prior to active analysis.

Still referring again to FIG. 3, in some embodiments, a fluid junction 40j can be used to connect the separation/transfer channel 25 and respective EO (electroosmotic) pump channel 40c. The fluid junctions can be nanojunctions with the associated nanojunction channels having nanometer-sized depths. These channels also typically have micrometer-sized widths. The nanojunctions 40j can have, for example, a depth of about 50 nm and a width of about 50 The depth of the nanochannel may be dictated by the ionic strength of the buffers used in the experiment/analysis and the corresponding Debye lengths. Nanochannel depth should be on the order of the Debye length or smaller.

Figures 4A, 4B, 4C:
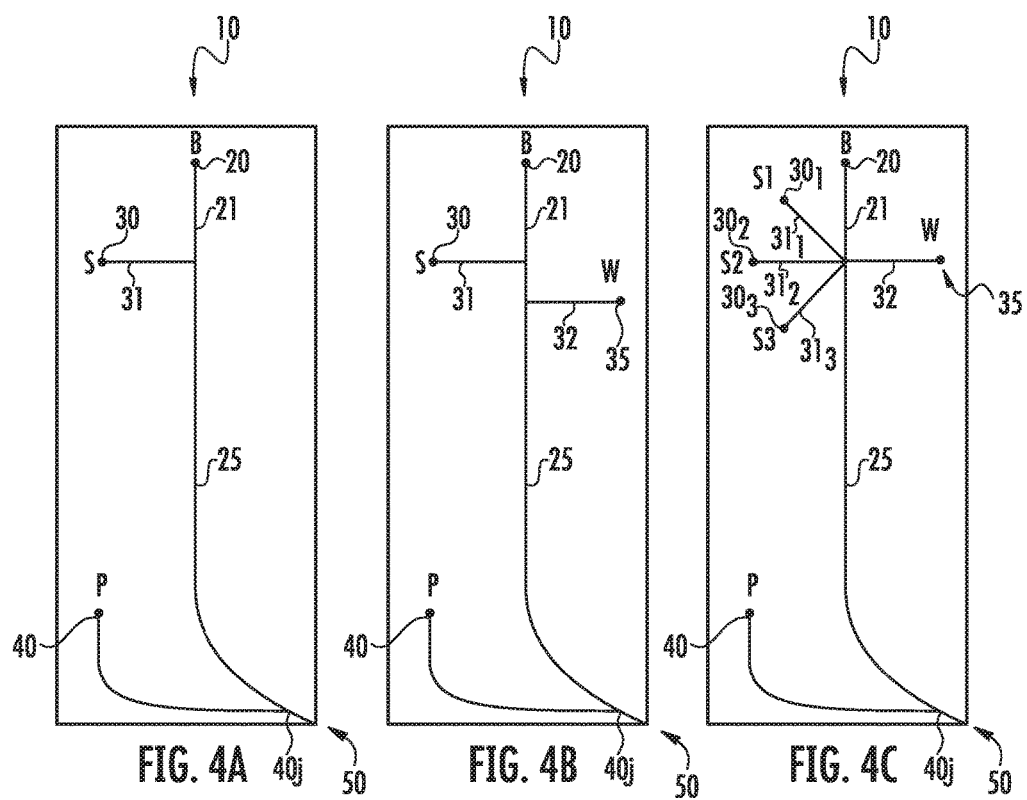
FIGS. 4A-4E are schematic illustrations of microfluidic devices that can be configured for pressure-driven injection according to embodiments of the present invention.

FIGS. 4A-4E are non-limiting examples of microfluidic devices 10 that can be operated as described above. FIG. 4A illustrates the microfluidic device 10 does not require a waste channel 32 or waste reservoir 35. FIG. 4B illustrates the waste channel 32 offset a longitudinal distance from the sample channel 31 across the separation channel 25. FIG. 4C illustrates the device 10 can have a plurality of sample reservoirs 30, shown by way of example as three, $30_1$, $30_2$, $30_3$, but more or less than three may be used. The sample reservoirs 30 can feed a common or different sample channels 31, shown as having different sample channels $31_1$, $31_2$, $31_3$ all for a single separation channel 25, and at least one BGE reservoir 20 (shown as a single BGE reservoir 20 and reservoir channel 21). The sample reservoirs 30 can be controlled to sequentially or serially be pressure-driven to inject respective plugs into the separation channel 25. The devices 10 can also have an EO pump 40.

Figure 4D:
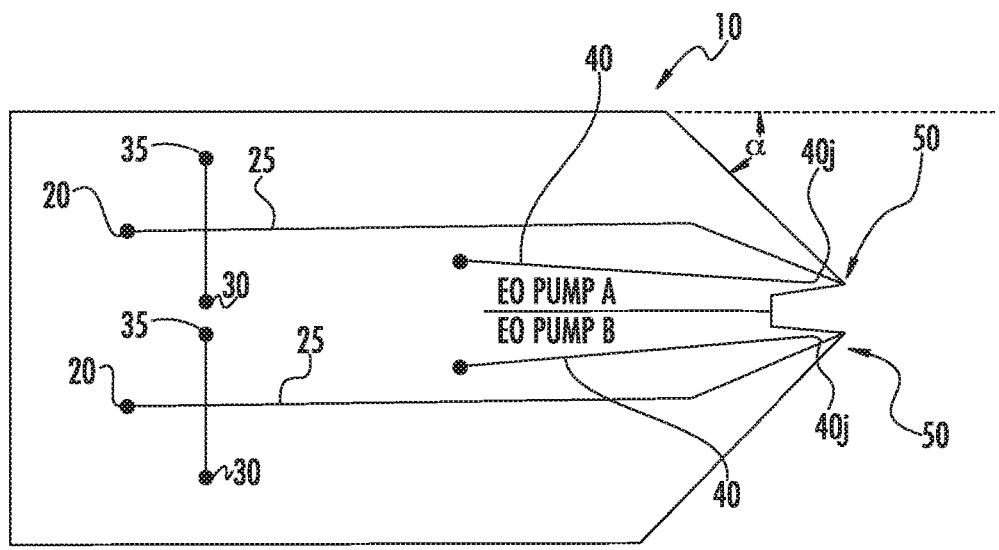

FIG. 4D illustrates a microfluidic device 10 that can have a plurality of separation channels 25, shown as two adjacent channels, but more than two may be included on a single device 10. The separation channels 25 can feed a common or separate emitters 50. Thus, he microfluidic device 10 can include more than one separation channel and associated BGE reservoir 20, sample reservoir 30, waste reservoir 35 and cross channels 31, 32. One or more of the individual channels 21, 25, 31, 32 might be configured to have lateral dimensions of about 1-100 µm, e.g., about 75 µm, with lateral spaced apart dimensions of about 1-100 mm, in some particular embodiments.

Figure 4E:
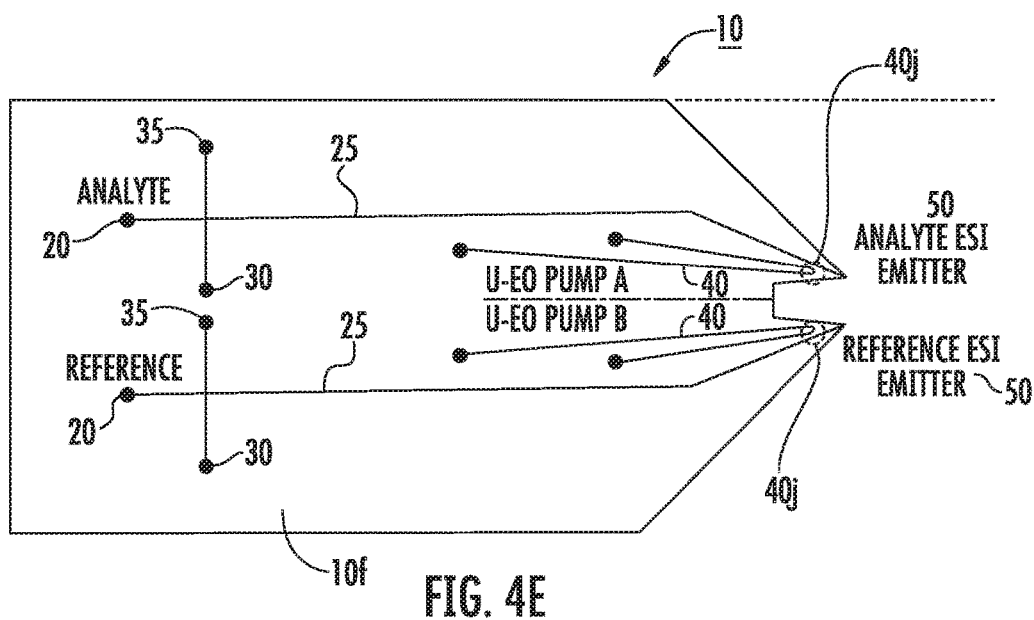

As shown in FIG. 4E, one or more reference channels for a reference spray may be included on/in the microfluidic device 10. Where used, the reference material for the reference spray from a respective ESI emitter 50 can provide one or more ions for internal calibration. In some embodiments, the reference material provides a single defined ion for internal calibration. In other embodiments, the reference material can include multiple ions over a desired range, typically that are over substantially an entire m/z range of interest, to improve the mass accuracy.

Figure 5:
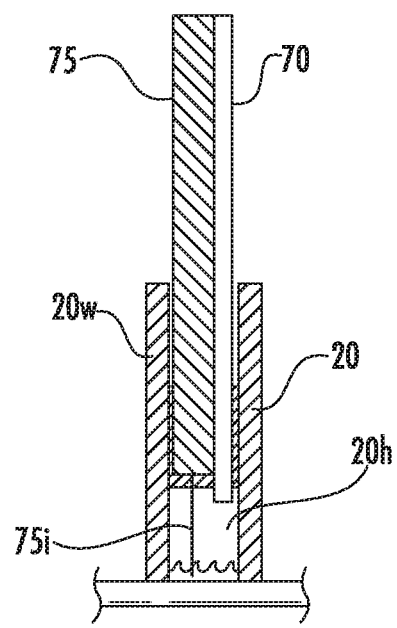
FIG. 5 is a schematic illustration of an example of a gas-tight connection with a pressurized supply line for the background electrolyte (BGE) reservoir according to embodiments of the present invention.

FIG. 5 is a schematic illustration of a BGE reservoir 20 having a gas-tight fitting holding a pressure supply line 70 and a high voltage line 75 with a high voltage input 75$i$ (shown as a platinum wire) that extends inside the sealed reservoir 20 so as to be able to make contact with the fluid, e.g., liquid, in the reservoir 20. The term "gas-tight" means that the seal on the reservoir 20, 30 does not unduly leak when operated so as to be able to provide the desired pressure to the headspace 20$h$, 30$h$ for pressure-driven injection.

Figure 6:
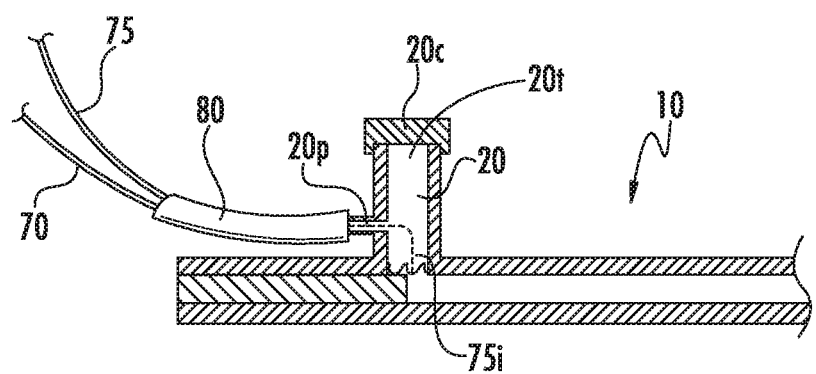
FIG. 6 is a schematic illustration of another example of a gas-tight connection with a pressurized supply line for the background electrolyte (BGE) reservoir according to embodiments of the present invention.

The pressure supply line 70 can be provided with tubing with an open pressurized gas path extending into the sealed headspace 20$h$. For an example of an 8 mm inner diameter reservoir wall 20$w$, the pressure supply line can be tubing less than this size, e.g., ¼ inch to about 1/16 inch outer diameter. However, larger size conduits can be used when stepped down in size for the supply into the reservoir head space under the sealed connection. The sealed (e.g., gas-tight) connection of a respective pressurized gas supply line 70 to either reservoir 20, 30 can be provided via epoxy, O-ring, metal or elastomeric gaskets, grease fittings, and/or other suitable configurations. FIG. 6 illustrates that the pressured gas supply line 70 can be held adjacent the high voltage cable 75 in a common sleeve 80. It is further noted that the high voltage cable 75 can be held routed into the headspace while held inside the gas supply tubing.

FIG. 6 also illustrates that the top of the reservoir 20$t$ can be sealed with a cap 20$c$ and a side port 20$p$ can be used to attach the pressurized gas supply line 70 to the reservoir 20. The same arrangement can be used for the sample reservoir 30 (not shown). In some embodiments, the gas supply line 70 can be attached over the outer wall of the wall 20$w$ of the reservoir 20 instead of extending inside the reservoir 20 for gas-tight or sealed connection. Other connection configurations may be used.

FIG. 7A illustrates an example of a microfluidic system 100 which includes a controller 100$c$ used to control operation of the pressure supply to the reservoirs 20, 30 to carry out the pressure-driven injection. The system 100 can include first and second pressurized gas supply lines or conduits 70, shown as 70$_1$, 70$_2$, each in fluid communication with at least one valve 120, 130. The system 100 can include a single three-way valve (FIG. 7B) that closes and opens each supply line. However, in preferred embodiments, separate valves 120, 130 are used for each supply line 70$_1$, 70$_2$. One or both of the valves 120, 130 can be a three-way valve (e.g., three way operation, open/close to source, open/close to head space and open/close to atmosphere) for a respective supply line 70 which can allow for the rapid venting of pressurized gas from a respective supply line. Thus, in operation, one or both of the valves 120, 130 can be operated to vent the head pressure in the reservoir 20, 30, to atmosphere, which may help precisely control the injection process. One or both of the gas supply lines 70 and/or reservoirs 20, 30 can also or alternatively include vents (121, 131) that can be electronically opened and closed, for rapid venting to atmosphere to decrease pressure in a respective headspace 20$h$, 30$h$. The term "rapid" with respect to the venting or pressure reduction (e.g., venting to atmosphere) in a respective pressure supply line 70 refers to a drop in pressure of the corresponding headspace 20$h$, 30$h$ of a respective reservoir 20, 30 to at least atmospheric pressure within 0.1-3 seconds, more typically within about 2 seconds or within about 1 second. The rapid venting can be based on a control signal from the controller 100$c$ that (a) directs the valve 120 or 130 to open to atmosphere (where a three-way valve is used) or (b) opens a vent separate from the valve 120, 130 and closes the valve 120, 130. The rapid pressure reduction (e.g., venting) can be measured by a pressure sensor in the supply line or reservoir to indicate the rapid drop in head pressure from an operative pressure to atmospheric pressure within a 0.1-2 second time period. In some embodiments, the rapid venting can be carried out in between about 0.1 seconds and 1.5 seconds, such as about 0.1 seconds, about 0.2 seconds, about 0.3 seconds, about 0.4 seconds, about 0.5 seconds, about 0.6 seconds, about 0, 7 seconds, about 0.8 seconds, about 0.9 seconds, about 1 second, about 1.1 seconds, about 1.2 seconds, about 1.25 seconds, about 1.5 seconds, about 2 seconds, and about 2.5 seconds.

The first and second pressurized gas supply lines 70$_1$, 70$_2$ can each be in communication with a common pressurized gas source 90 or each may have its own pressurized gas source. The system 100 can include a power supply 95 for the high voltage input to the microfluidic device 10. The power supply 95 can be attached to the cable 75.

The controller 100$c$ can direct the timing sequence of the differentially applied pressure to the microfluidic device. The controller 100$c$ can be in communication with the valves 120, 130, the at least one pressure source 90 and the power supply 95. The term "controller" is used broadly to include a single or multiple processors or application specific integrated circuit (ASIC) held on a single device, e.g., the microfluidic device 10, and/or computer, laptop, notebook, smartphone and the like, or distributed in different devices using wires or wireless connections including local area networks or wide area networks, e.g., the internet, including any server system.

Figure 8:
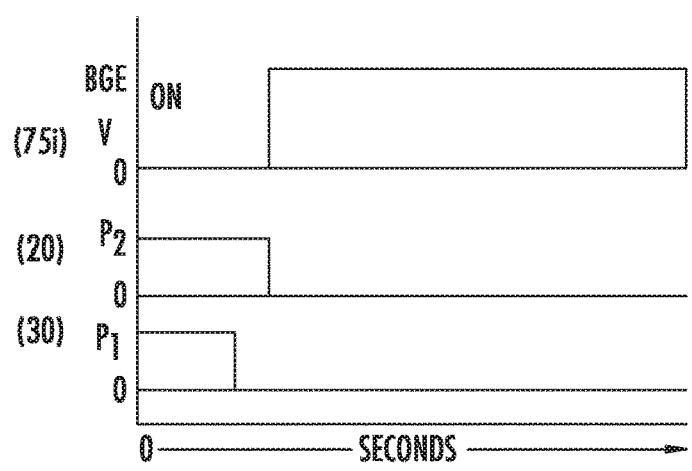
FIG. 8 is an example of a timing chart for the pressures applied to the sample and BGE reservoirs for injecting a sample in to a separation channel according to embodiments of the present invention.

The controller 100$c$ can direct the first and second valves 120, 130 to open and close to carry out successive sample injection and electrophoretic separation using a defined sequence, an example of which is shown in the timing chart of FIG. 8. It is noted that the electrophoretic separation voltage can be applied concurrently with or just after pressure P2 is removed or decreased from the BGE reservoir 20. As shown, sample injection is carried out using only pressure P1 applied to the BGE reservoir and only pressure P2 applied to the sample reservoir from the first and second supply lines 70 (e.g., tubes or conduits) without any electrokinetic (EK) voltage. Voltage can be applied to the BGE reservoir 20 after the injection (FIG. 1C).

The controller 100$c$ can be configured to operate the microfluidic device 10 using a defined timing sequence for applying defined pressures (headspace pressures) between 0.1 and 30 psi to a headspace 20$h$ of the BGE reservoir 20 via the supply tube 70$_2$ and to a headspace 30$h$ of the sample reservoir 30 via the supply tube 70$_1$ for defined durations, typically between 1 and 10 seconds, to inject a sample into the separation channel 25. The timing chart shown in FIG. 8 is by way of example and the noted "zero" pressures of P1 (for the sample reservoir 30) and P2 (for the BGE reservoir 20) may be atmospheric or ambient pressures or may alternatively be vacuum pressures. The applied voltage V from the power supply 95 to the input 75*i* in the BGE reservoir 20 (top line of the timing chart in FIG. 8) can have a shorter or longer duration than the concurrent injection pressures P1, P2 (FIG. 1A) or the subsequent "clearing" pressure P2 (FIG. 1B). The P2 pressure can remain constant or change, typically decreasing, from the concurrent pressure for injection to the "clearing" pressure when P1 is "OFF" or substantially decreased (FIG. 1B).

The microfluidic device 10 can be a microfluidic chip that is formed of hard or substantially rigid materials that include, but are not limited to, substrates comprising one or combinations of: glass, quartz, silicon, ceramic, silicon nitride, polycarbonate, and polymethylmethacrylate. In particular embodiments, the device 10 can include a glass substrate such as a borosilicate. In other embodiments, a rigid polymer material may be used to form the microfluidic device. The device 10 can also include one or more layers of a soft or flexible substrate. Soft substrate materials, where used, can have a low Young's Modulus value. For example, elastomers and harder plastics and/or polymers can have a range between about 0.1-3000 MPa. Examples of soft materials include, but are not limited to, polydimethylsiloxane (PDMS), polymethylmethacrylate (PMMA), and polyurethane. See, e.g., co-pending PCT/US2012/027662 filed Mar. 5, 2012 and PCT/US2011/052127 filed Sep. 19, 2011 for a description of examples of microfabricated fluidic devices. See, also, Mellors, J. S.; Gorbounov, V.; Ramsey, R. S.; Ramsey, J. M., Fully integrated glass microfluidic device for performing high-efficiency capillary electrophoresis and electrospray ionization mass spectrometry. *Anal Chem* 2008, 80 (18), 6881-6887. For additional information that may be useful for some designs, see also, Xue Q, Foret F, Dunayevskiy Y M, Zavracky P M, McGruer N E & Karger B L (1997), Multichannel Microchip Electrospray Mass Spectrometry. *Anal Chem* 69, 426-430, Ramsey R S & Ramsey J M (1997), Generating Electrospray from Microchip Devices Using Electroosmotic Pumping. *Anal Chem* 69, 1174-1178, Chambers A G, Mellors J S, Henley W H & Ramsey J M (2011), Monolithic Integration of Two-Dimensional Liquid Chromatography—Capillary Electrophoresis and Electrospray Ionization on a Microfluidic Device. *Analytical Chemistry* 83, 842-849. The contents of these documents are hereby incorporated by reference as if recited in full herein.

EO pumps can be integrated on a microfluidic device 10 for electrospray ionization via implementations other than the examples shown in FIG. 3 or 4A-4E. The basic requirement is to have two channels intersect at a junction, which may be a T-like junction (not restricted to a right angle intersection). A voltage is applied to two of the three resulting channel termini generating an axial electric field through the associated channel segments. To realize hydraulic transport through the third channel segment, the electroosmotic mobility in the two channel segments that contain the axial electric field is generally different in magnitude and/or sign. The difference in electroosmotic mobility can be achieved by chemically modifying one, or both, of the associated channel segments so as to produce different surface charge densities and hence different electroosmotic mobilities. Electroosmotic mobility can also be modified by coating a channel wall with electrically neutral polymer films, thereby increasing the effective fluid viscosity within the electrical double layer at the wall. Another way to modify electroosmotic mobility is reduce one of the channel lateral dimensions to distances similar in magnitude to the Debye length of the solution being electroosmotically pumped. The described methods for modifying electroosmotic mobility may also be used in combination where desired. Methods for electroosmotic pumping are further described in U.S. Pat. No. 6,110,343, the contents of which are hereby incorporated by reference.

While it is convenient to monolithically integrate EO pump functional elements on electrospray microfluidic devices, it is possible to hydraulically deliver sample materials to the emitter. See, e.g., Chambers A G, Mellors J S, Henley W H & Ramsey J M (2011) Monolithic Integration of Two-Dimensional Liquid Chromatography—Capillary Electrophoresis and Electrospray Ionization on a Microfluidic Device. *Analytical Chemistry* 83, 842-849. When utilizing hydraulic transport to supply analyte to the emitter, electrical connection for producing the electrospray, voltage can be achieved using a side channel similar to the EO pumping channel or by contacting the fluid using an electrode in a reservoir external to the microfluidic device, or in the case of using metal tubing between the device 10 and the pump, connection can be made to the tubing.

FIGS. 9A and 9B schematically illustrate embodiments of the invention. FIG. 9A illustrates a portable mass spectrometer 200 with a housing 201 holding at least one of the microfluidic devices 10 with an onboard controller 100*c*, a power supply for the voltage 95, a pressurized gas supply 90, a detector 205, an analyzer 210 and an optional display 215 for providing output data.

FIG. 9B illustrates that the microfluidic device 10 can be in communication with a mass spectrometer 200. The controller 100*c* can be separate or partially or totally onboard the mass spectrometer 200.

Figure 10:
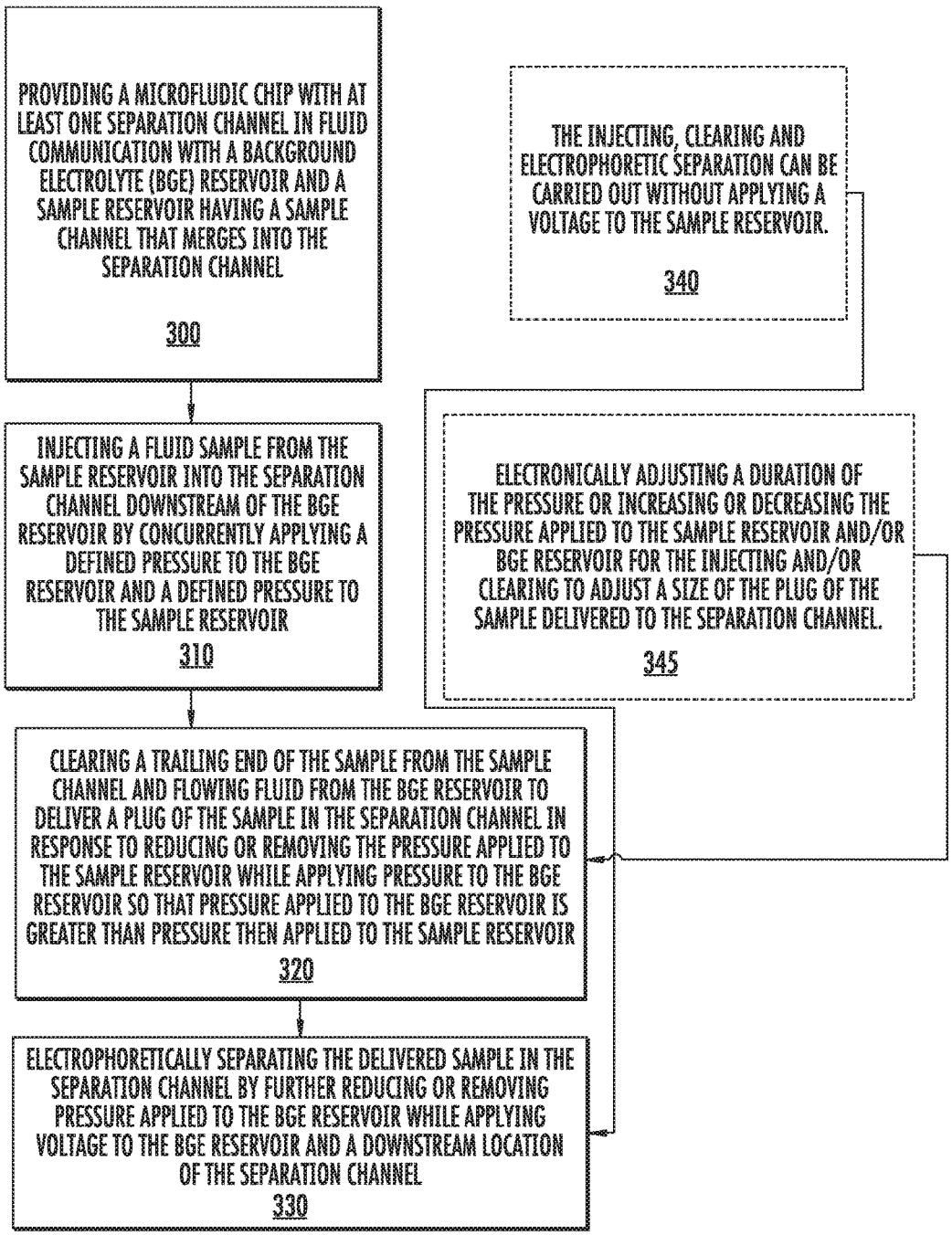
FIG. 10 is a flow chart of exemplary operations that can be used to carry out embodiments of the present invention.

FIG. 10 is a flow chart of exemplary operations that can be used to carry out a sample analysis. A microfluidic device is provided with at least one separation channel in fluid communication with a background electrolyte (BGE) reservoir and a sample reservoir and having a sample channel that merges into the separation channel (block 300). A fluid sample is injected from the sample reservoir into the separation channel downstream of the BGE reservoir by concurrently applying a defined pressure to the BGE reservoir and a defined pressure to the sample reservoir (block 310). Then, a trailing end of the sample is cleared from the sample channel and fluid is flowed from the BGE reservoir to deliver a plug of the sample in the separation channel in response to reducing or removing the pressure applied to the sample reservoir while applying pressure to the BGE reservoir so that pressure applied to the BGE reservoir is greater than pressure then applied to the sample reservoir (block 320). Then, the delivered sample is electrophoretically separated in the separation channel by applying voltage to the BGE reservoir and a downstream location of the separation channel (block 330). The pressure in the BGE reservoir can be held constant, further reduced or removed while the voltage is applied.

The injecting, clearing and electrophoretic separation can be carried out without applying a voltage to the sample reservoir (block 340).

A duration of the pressure can be electronically adjusted or the pressure applied to the sample or BGE reservoir 20, 30 can be increased or decreased for the injecting and/or clearing to adjust a size of the plug of the sample delivered to the separation channel (block 345).

It is noted that embodiments of the present invention may combine software, firmware and/or hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

Figure 11:
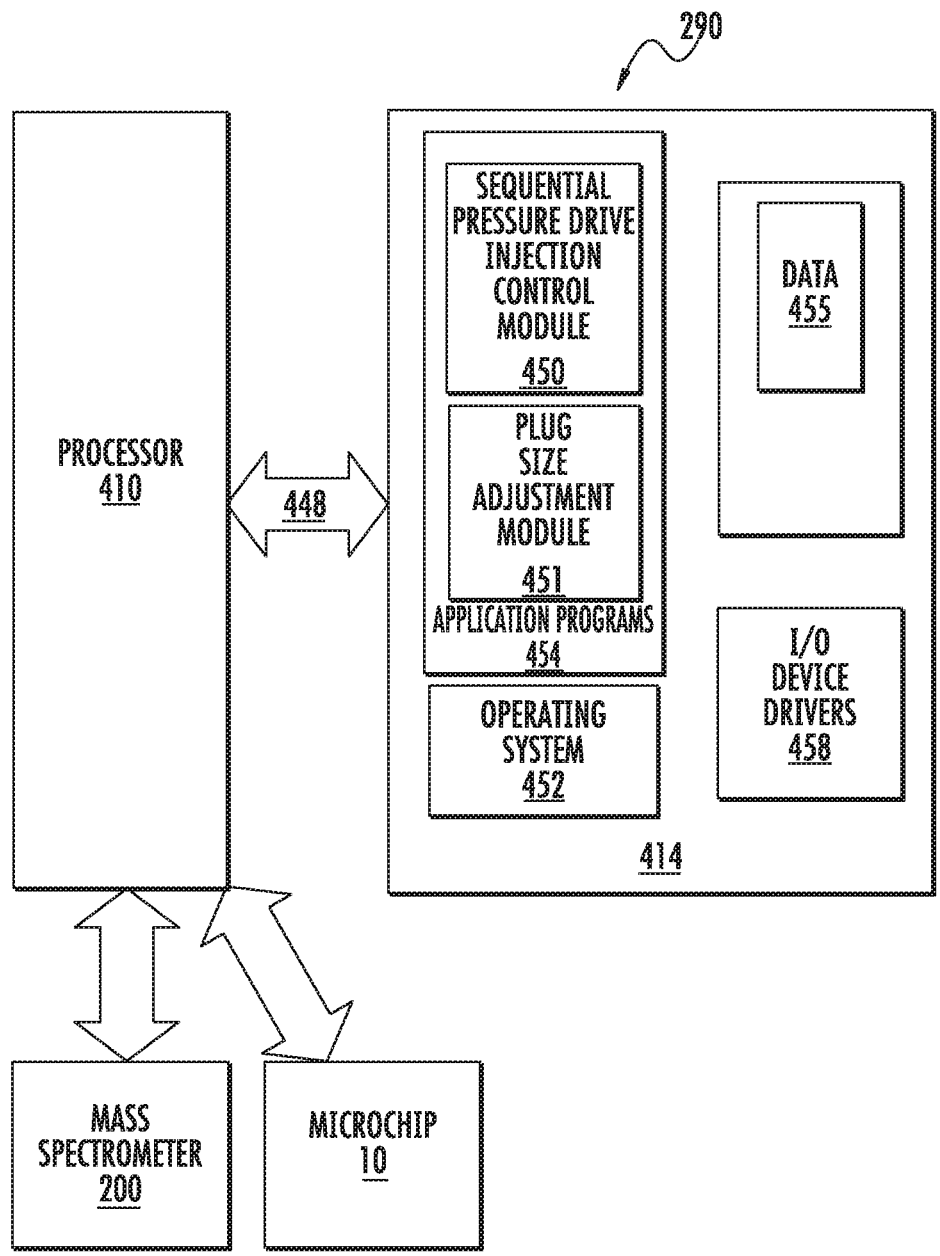
FIG. 11 is a block diagram of a data processing system according to embodiments of the present invention.

FIG. 11 is a schematic illustration of a circuit or data processing system 290. The system 290 can be used with microfluidic devices 10 and/or mass spectrometers 200. The circuits and/or data processing systems 290 may be incorporated in a digital signal processor in any suitable device or devices. As shown in FIG. 11, the processor 410 can communicate with a mass spectrometer 200 and/or microfluidic device 10 and with memory 414 via an address/data bus 448. The processor 410 can reside in a control circuit or controller that is separate from the spectrometer 200 or that is integrated wholly or partially therein. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 11 illustrates that the memory 414 may include several categories of software and data used in the data processing system: the operating system 452; the application programs 454; the input/output (I/O) device drivers 458; and data 455. The data 455 can include sample type, plug size adjustments for pressures, calibration data, time synchronization data (e.g., pressures/duration for loading/injection), and/or other detected or internal mass spectrometer data.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Sequential Pressure Drive Injection Control Module 450 and the Plug Size (pressure/duration) Adjustment Module 451 being application programs in FIG. 11, as will be appreciated by those of skill in the art, other configurations may also be utilized while still benefiting from the teachings of the present invention. The Module 451 can allow for a user to select a desired injection time (Pressure ON time, OFF time, pressure for a respective injection and/or clearing and the like, for each reservoir). The Module 450 and/or 451 may also be incorporated into the operating system 452, the I/O device drivers 458 or other such logical division of the data processing system. Thus, the present invention should not be construed as limited to the configuration of FIG. 11, which is intended to encompass any configuration capable of carrying out the operations described herein. Further, Module 450 and/or 451 can communicate with or be incorporated totally or partially in other components, such as a mass spectrometer 200, power supply 95, an interface/gateway or a computer such as at a workstation that may be local or remote from the microfluidic device/spectrometer.

The I/O data port can be used to transfer information between the data processing system, the workstation, the spectrometer, the microfluidic device, the interface/gateway and another computer system or a network (e.g., the Internet) or to other devices or circuits controlled by the processor. These components may be conventional components such as those used in many conventional data processing systems, which may be configured in accordance with the present invention to operate as described herein.

The present invention is explained in greater detail in the following non-limiting Examples.

EXAMPLES

Microchip CE with integrated ESI for MS detection was used for the analysis of amino acids. The new pressure-driven injection method was compared to the commonly used electrokinetic (EK) gate method (using the methodology described in FIGS. 1A-1C and 2A-2C) using the microfluidic device shown in FIG. 3. This type of microchip CE-ESI device has been described previously and is commonly used in lab settings. For all of the data presented here, the sample contained a 10 μM mixture of the 20 essential amino acids. The salt content of the samples was varied to illustrate the superior salt tolerance of the new injection method and also to illustrate the phenomenon of transient isotachophoresis (tITP) that is allowed by the new pressure-driven injection method. All separations were performed with a separation field strength of approximately 1000 V/cm with a background electrolyte (BGE) of 50% methanol, 2% formic acid (pH 2.2). Computer control of voltages applied to the microfluidic device was accomplished using previously described methods. For the new pressure-driven injection method, a pressure of 2 psi was applied to the head space of the sample and BGE reservoirs. The pressure was controlled using one 3-way electronic valve (Clippard) for each of these two reservoirs. The valves were controlled using the same computer control system used to supply high voltage to the microfluidic device. Gas tight connections were made to the microfluidic reservoirs using PTFE tubing with an internal diameter equal to the diameter of the glass cylinders used as fluid reservoirs (8 mm) For the sample reservoir connection, the PTFE tubing was connected directly to the pressure supply line using a simple reducing union. The fitting used for the BGE reservoir is illustrated in FIG. 5. To allow the application of both high voltage and pressure, this fitting includes the high voltage electrode and a segment of 1/16 inch tubing which is coupled to a pressure supply line. For all of the data presented here, a Synapt G2 quadrupole-ion mobility-time of flight mass spectrometer (Waters Corp.) was used for detection and identification of the ions generated by the microchip CE-ESI device.

Figure 12A:
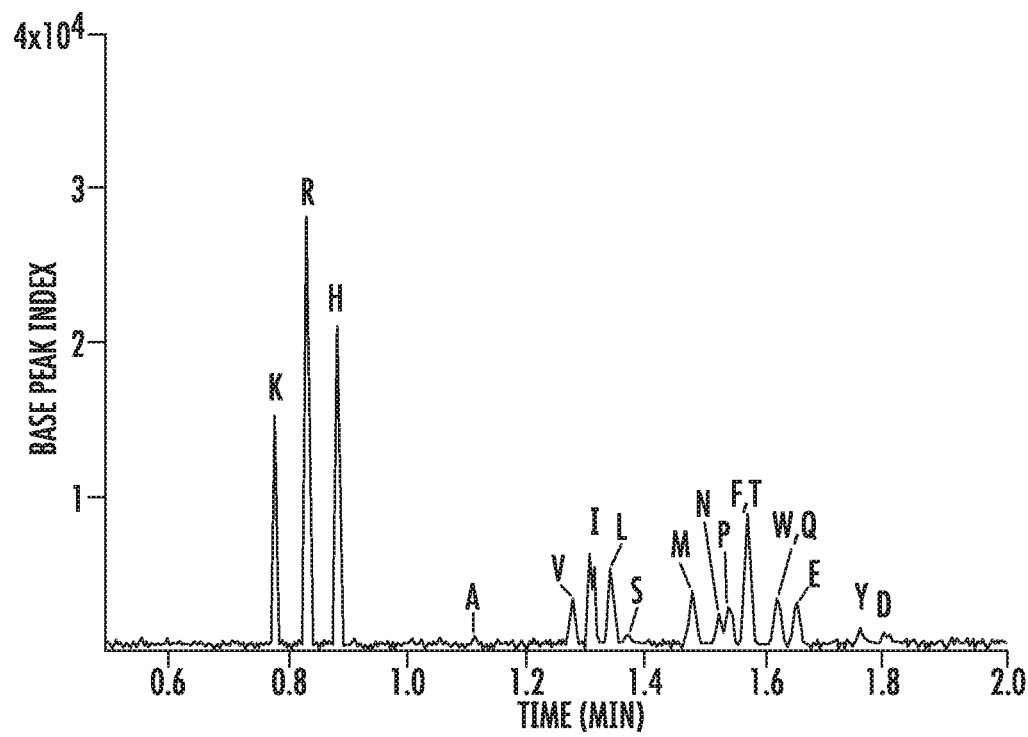
FIGS. 12A and 12B are electropherograms for the microfluidic CE-ESI-MS (Capillary Electrophoresis-Electrospray Ionization-Mass Spectrometry) analysis of the amino acid mixture prepared in BGE with no salt added.
Figure 12B:
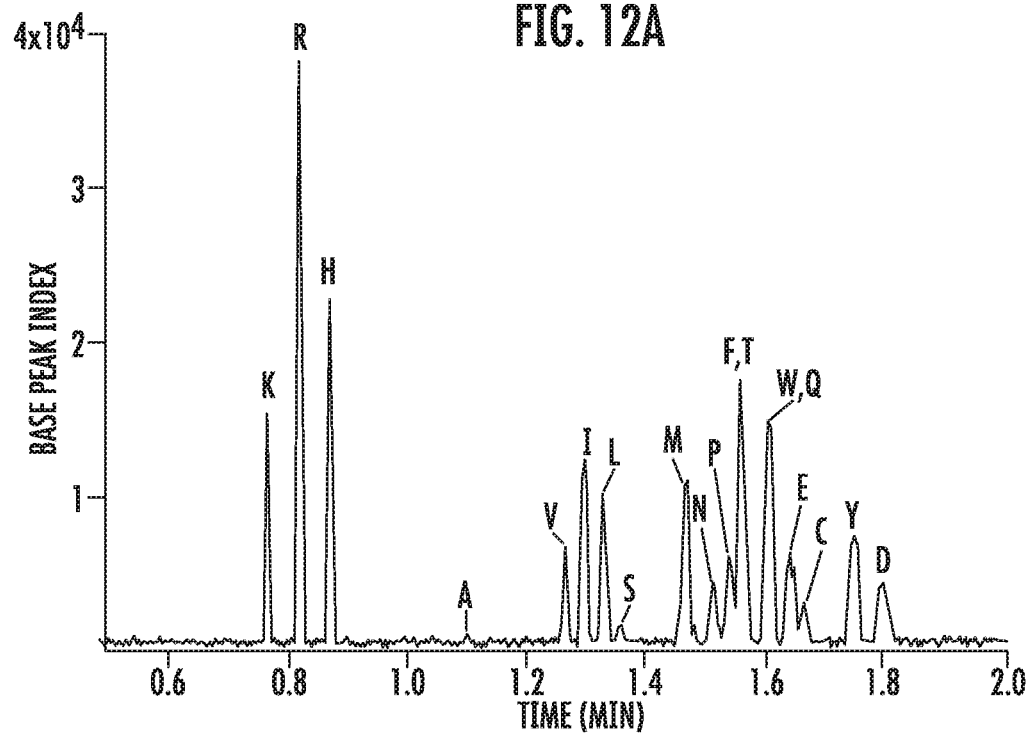

FIGS. 12A and 12B show electropherograms for the separation of sample with low salt content using both injection methods. The electropherograms are for the microfluidic CE-ESI-MS analysis of an amino acid mixture prepared in BGE with no salt added. For the pressure-driven injection (FIG. 12A), 2 psi was applied to both the sample and BGE reservoirs for 3 seconds, then just the BGE reservoir for 1 second. For the EK gated injection (FIG. 12A), the gate was opened for 0.2 seconds using the voltages shown in FIGS. 2A-2C. The effects of injection bias can be seen in FIG. 12A as relatively smaller peaks for the later eluting amino acids in the EK gated electropherogram. For the electrokinetic injection, injection bias causes the later eluting compounds to be significantly smaller. The new pressure driven injection method has no bias, so the peak areas are more consistent for all of the analytes. Differences in peak area for the pressure driven injection are caused purely by differences in the MS detector response for these different analytes.

Figure 13:
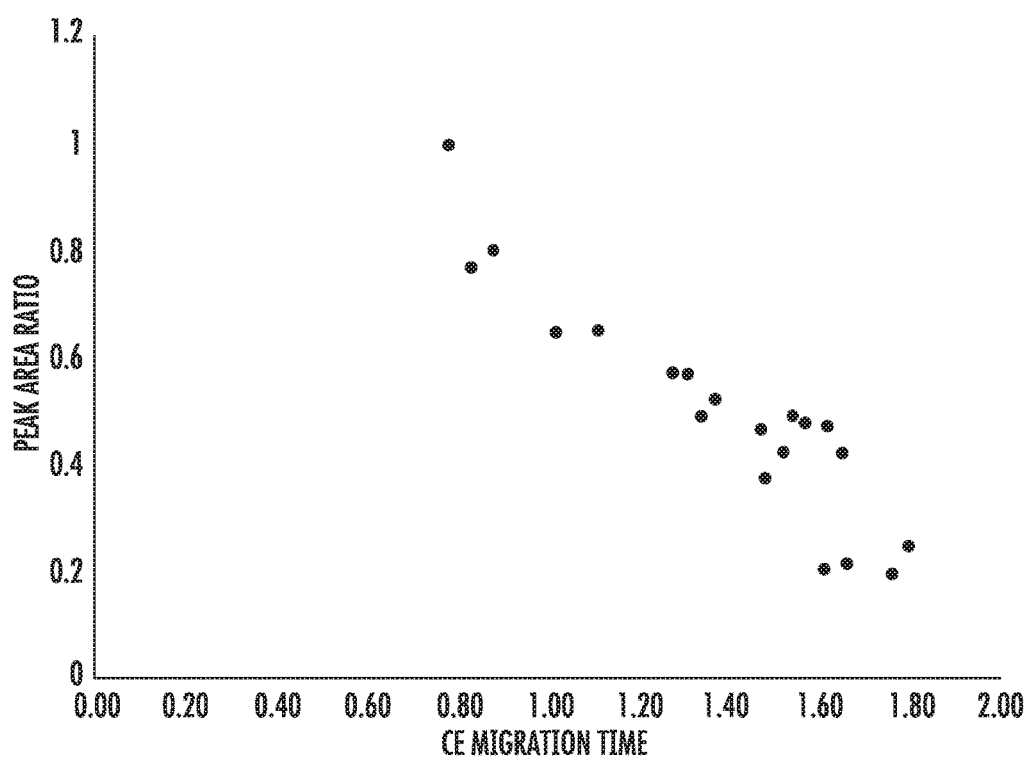
FIG. 13 is a graph of peak area ratio versus CE (capillary electrophoresis) migration time from the gated injection relative to peak areas from the new pressure-driven injection.

To illustrate this trend more clearly, the peak areas from the EK gated injection relative to the peak areas of the pressure driven injection are plotted in FIG. 13. The most mobile amino acid (lysine, K) had the same peak area using both injection methods. There is, however, a clear trend of decreasing relative peak area with longer migration times. The relative decrease in peak area as a function of migration time illustrates how analytes with slower electrophoretic mobility are biased against using the electrokinetically gated injection.

Injection method comparison for a sample with high salt content showed that the EK injection method had a more severe type of injection bias that can occur when the ionic strength of the sample is significantly greater than the ionic strength of the BGE. In this case, current flow from the sample reservoir to the separation channel is limited by the ionic conductivity of the BGE. An excess of ions from salt in the sample will prevent analyte ions from migrating into the separation channel. The end result is a severely biased injection when the ionic strength of the sample is significantly higher than the ionic strength of the BGE. This phenomenon places a major limitation on the utility of EK gated CE separations. The new pressure-driven injection method forces sample into the separation channel without regard for the electrical conductivity of the BGE, so analyte injection is not hampered by the salt content of the sample.

Figure 14A:
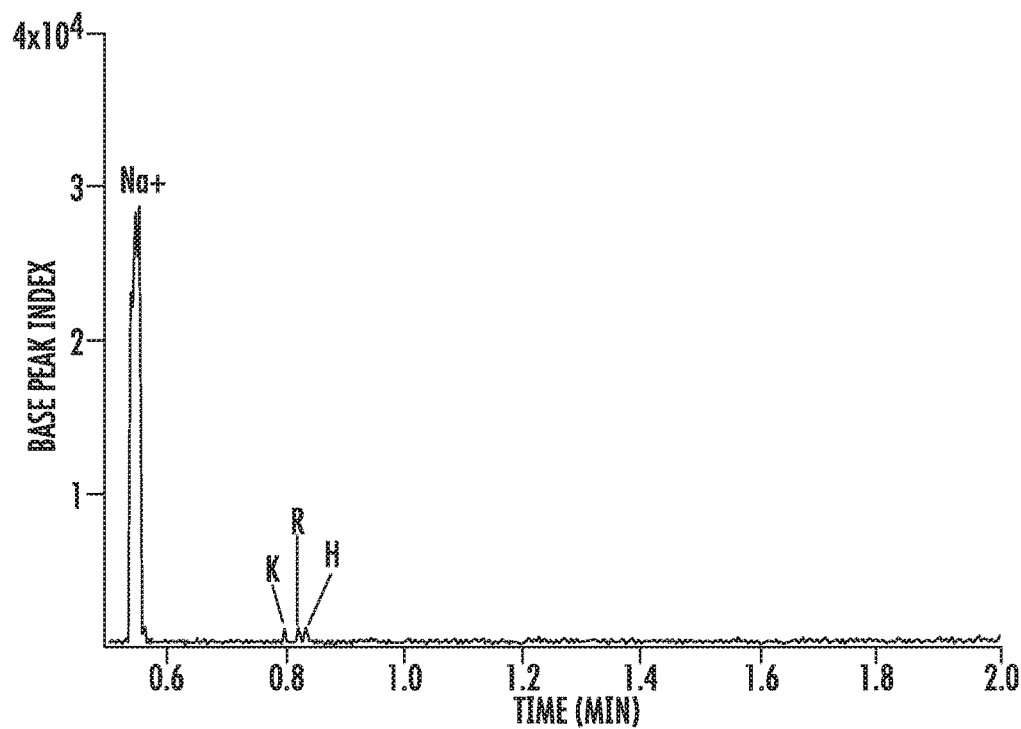
FIGS. 14A and 14B are electropherograms for the microfluidic CE-ESI-MS analysis of the amino acid mixture prepared in BGE with 100 mM sodium chloride added.
Figure 14B:
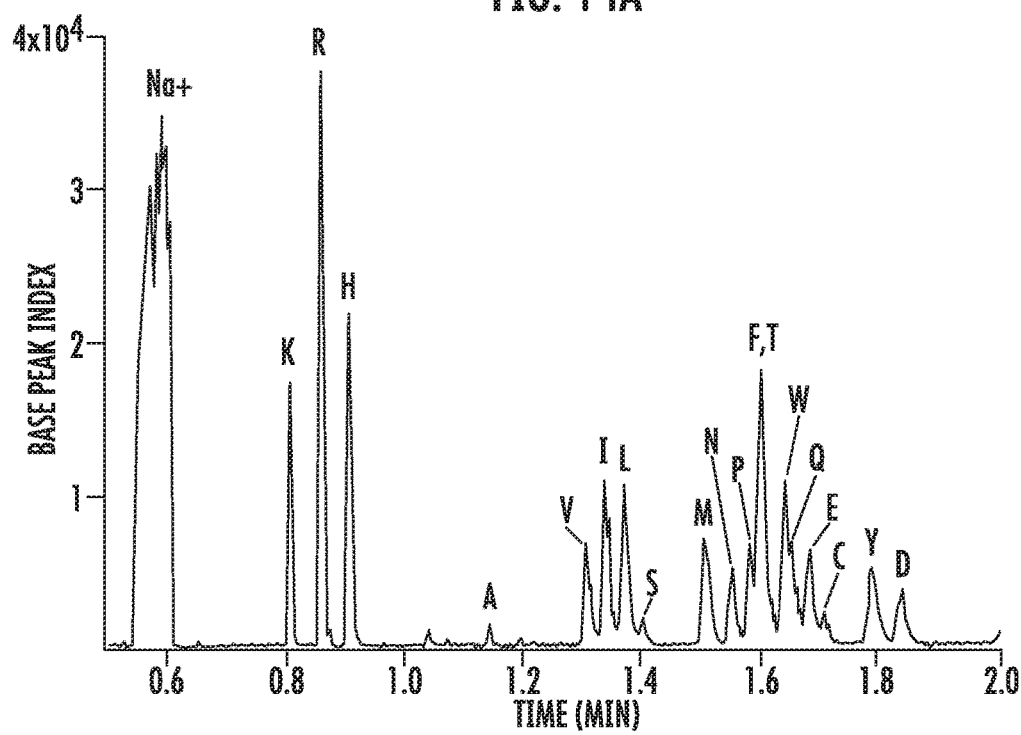

FIGS. 14A and 14B show electropherograms obtained from the analysis of a sample containing 100 mM sodium chloride using both injection methods. Sodium ions generate clusters of sodium formate during the electrospray process which can be detected by the mass spectrometer. For the EK injection (FIG. 14A), only the band of sodium and very small amounts of the highest mobility amino acids (K, R, and H) are detected. For the new pressure driven injection method (FIG. 14B), an even larger band of sodium is detected, but in this case all of the amino acids are also detected with similar intensity to the injection of the non-salty sample shown in FIG. 12B.

The use of salt in the sample for transient isotachophoresis was analyzed. The ability to position a well-defined band of sample into the separation channel of the microfluidic device using pressure-driven flow now allows the use of online sample focusing methods that are not possible by other microfluidic injection methods. Transient isotachophoresis (tITP) has been previously described as an online sample focusing method for capillary electrophoresis. This phenomenon works when the sample contains a relatively large concentration of an electrolyte (termed the leading electrolyte) that has higher electrophoretic mobility than the analyte ions. This is exactly the situation that exists for the pressure-driven injection of samples with high concentration of sodium chloride described above. To take advantage of the sample focusing effects of tITP a larger band of this sample need only be injected. This new injection method allows complete freedom in altering the size of the sample band, simply by changing the head pressure or the duration of the sample loading step. For the results presented in FIGS. 15A and 15B, the duration of the sample loading step was altered, while holding constant all other variables.

Figure 15A:
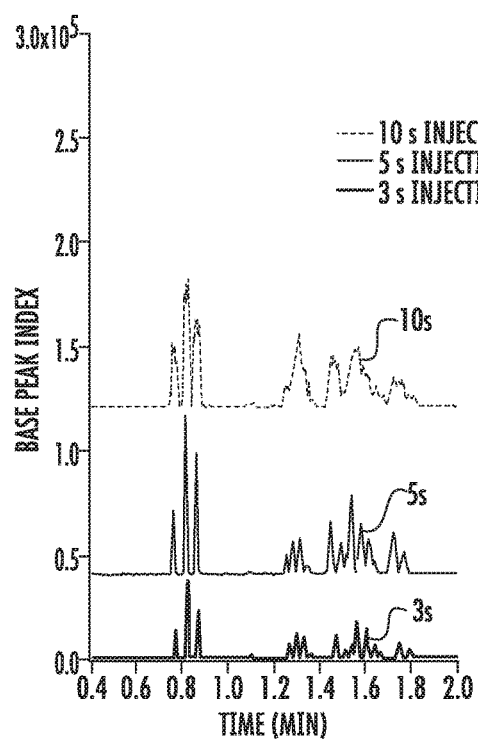
FIGS. 15A and 15B are electropherograms of base peak index over time for different injection times (3 seconds, 5 seconds and 10 seconds).
Figure 15B:
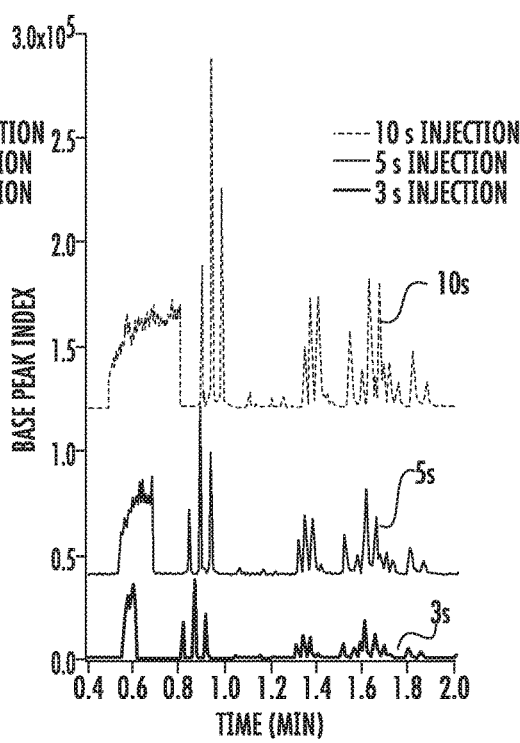

FIGS. 15A and 15B show how tITP yields sharp bands of increasing concentration when larger amounts of samples containing a sufficient concentration of leading electrolyte are injected. The electropherograms on the left (FIG. 15A) show how the analyte bands simply become wider for longer injection times without tITP. This sample contained no added salt to the BGE. The electropherograms on the right (FIG. 15B) show how the analyte bands focus into narrow bands of increasing concentration when tITP is occurring. The only difference between the two sets of runs was the addition of 100 mM sodium chloride to the sample used for the runs shown on the right (FIG. 15B). Sodium can also be seen in the data on the right as a wide band that elutes before the amino acids. This clearly shows how the leading electrolyte band does not focus during tITP while the less mobile analyte ions focus into sharp peaks. The effect of salt content on microchip tITP-CE-ESI-MS was based on a mixture of 20 amino acids (10 uM). The electropherograms on the right show how tITP leads to sharp peaks of increasing concentration when larger amounts of a sample containing a sufficient concentration of leading electrolyte are loaded. This sample contained 100 mM sodium chloride. These injections were performed with a head pressure of 2 psi applied to the sample reservoir for the times labeled. All other conditions were identical for all of the electropherograms displayed here.

Figure 16A:
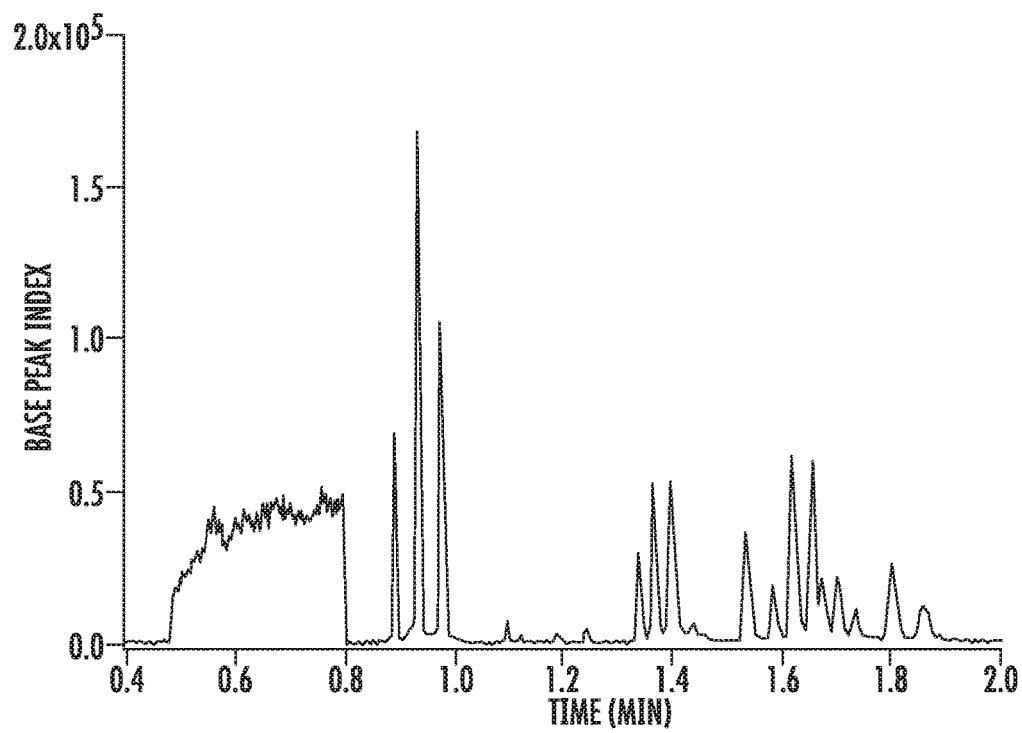
FIGS. 16A and 16B are electropherograms for tITP-CE-ESI-MS separations of amino acids with two different leading electrolytes added to the sample.
Figure 16B:
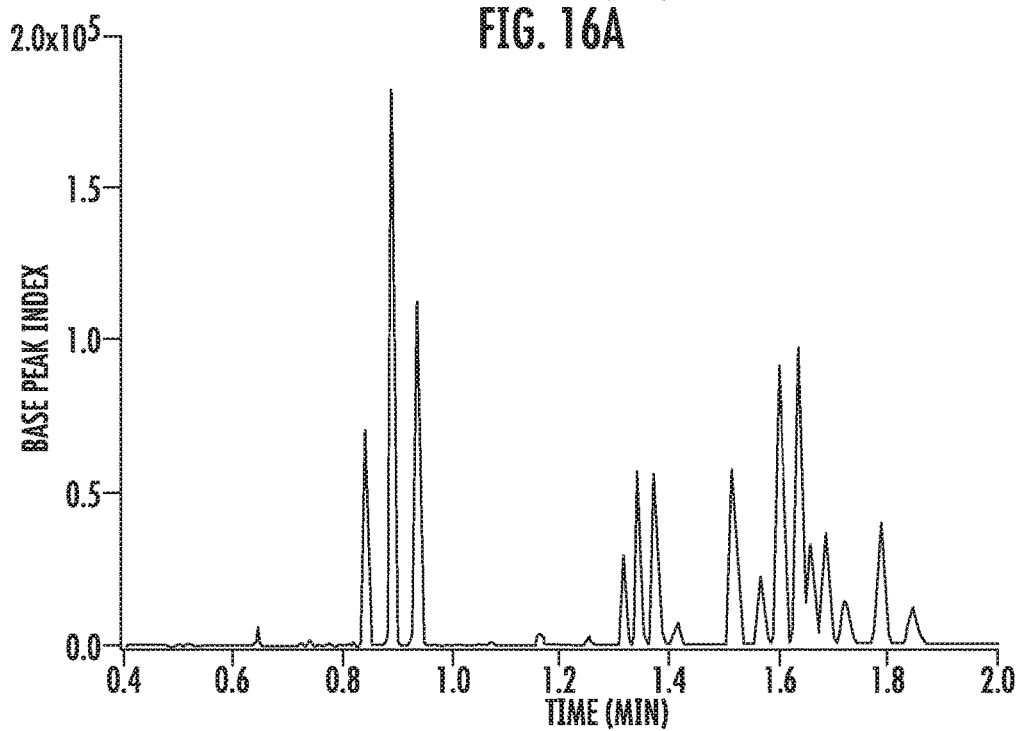

While 100 mM sodium chloride yields satisfactory results for tITP-CE-ESI-MS, other electrolytes can be used. Better separation performance can be achieved by using ammonium acetate instead of sodium chloride. FIGS. 16A and 16B show electropherograms from two tITP-CE-ESI-MS separations. Both samples were 10 μM amino acid mixtures injected for 10 seconds at 2 psi. The sample used for the top electropherogram (FIG. 16A) contained 100 mM sodium chloride, while the bottom (FIG. 16B) used 100 mM ammonium acetate. The sample injected with sodium chloride yielded abnormal peak shapes visible at the bottoms of the amino acid peaks, the peaks from the sample containing ammonium acetate had a much better shape. This improvement in peak shape yielded better resolution between neighboring peaks. Another clear difference is that ammonium ions yield a volatile salt during the ESI process, so they are not detected by ESI-MS like sodium. Ammonium is therefore less likely to cause fouling of the MS inlet electrodes. Ammonium ions also have a higher electrophoretic mobility than sodium ions. This allows the tITP process to occur more quickly yielding less migration time delay. This effect can be seen by comparing the migration time of the earliest eluting amino acid (lysine) in the two runs shown in FIGS. 15A/15B. The migration time was 3 seconds earlier for this example. The effect would be more significant for larger sample injection volumes.

The new pressure-driven injection method described allows (completely) unbiased injections of samples for microfluidic CE separations. These methods can be used to inject a cleanly-defined band of sample regardless of the sample composition. The size of the sample band can be precisely controlled simply by altering the pressure and/or duration of the injection. These traits make this injection method ideal for performing on-chip sample focusing methods such as transient isotachophoresis. A notable difference between this method and previously described methods is the application of pressure to two different solvent reservoirs with the ability to control those pressures independently using (typically off-chip) valves. This allows a precisely loaded sample into the separation channel and then clear extra sample from the side arms of the injection cross in only two discrete pressure-only driven steps.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method, comprising:
   initiating injection of a fluid sample from a first reservoir into a first channel of a fluidic device by applying a first pressure to the fluid sample in the first reservoir, thereby causing at least a portion of the fluid sample to enter the first channel; and
   terminating injection of the fluid sample by applying a second pressure to a background fluid in a second reservoir, thereby causing background fluid to flow in a uniform direction within the first channel,
   wherein no electrical potential is applied across the fluid sample to inject the sample into the first channel.

2. The method of claim 1, wherein the second pressure is larger than the first pressure when injection of the fluid sample is terminated.

3. The method of claim 1, further comprising terminating application of the first pressure to the fluid sample when the second pressure is applied to the background fluid.

4. The method of claim 1, further comprising:
   during a first portion of an injection period for the fluid sample, applying the first pressure to the fluid sample in the first reservoir; and
   during a second portion of the injection period, applying the second pressure to the background fluid in the second reservoir and applying a third pressure to the fluid sample in the first reservoir,
   wherein the third pressure is less than the second pressure.

5. The method of claim 4, wherein a difference between the third pressure and an ambient pressure external to the first reservoir is zero.

6. The method of claim 4, further comprising, during the first portion of the injection period, applying a fourth pressure to the background fluid in the second reservoir.

7. The method of claim 6, wherein a difference between the fourth pressure applied to the background fluid and an ambient pressure external to the second reservoir is between 0.5 psi and 10 psi.

8. The method of claim 6, wherein the first and fourth pressures are applied for between 1 second and 5 seconds.

9. The method of claim 6, wherein the second and third pressures are applied for 2 seconds or less.

10. The method of claim 6, wherein the second pressure is at least 10% less than the fourth pressure.

11. The method of claim 6, wherein the second pressure is less than the fourth pressure by up to 80% of the fourth pressure.

12. The method of claim 1, further comprising, following injection of the fluid sample into the first channel, applying an electrical potential difference across the fluid sample in the first channel to electrophoretically separate components of the fluid sample in the first channel.

13. The method of claim 12, further comprising:
discharging the separated components of the fluid sample from the first channel and into a mass spectrometry system; and
analyzing the separated components using the mass spectrometry system.

14. The method of claim 1, wherein a difference between the first pressure applied to the fluid sample and an ambient pressure external to the first reservoir is between 0.5 psi and 10 psi.

15. The method of claim 1, wherein a difference between the second pressure applied to the background fluid and an ambient pressure external to the second reservoir is between 0.5 psi and 10 psi.

16. The method of claim 1, wherein applying the first pressure to the fluid sample comprises introducing a first gas into the first reservoir, and wherein applying the second pressure to the background fluid comprises introducing a second gas into the second reservoir.

17. The method of claim 16, wherein the first and second gases are the same.

18. The method of claim 1, wherein application of the first pressure to the fluid sample causes at least a portion of the fluid sample to flow in a first direction along a sample channel and to enter a fluid junction formed by an intersection of the sample channel and the first channel.

19. The method of claim 18, wherein application of the second pressure to the background fluid causes the at least a portion of the fluid sample in the fluid junction to leave the fluid junction and flow in a second direction in the first channel and downstream from the fluid junction.

20. The method of claim 19, wherein the first direction is orthogonal to the second direction.

21. A sample analysis system, comprising:
a fluidic chip comprising a first fluid reservoir, a second fluid reservoir, and a first channel in fluid communication with the first and second fluid reservoirs;
a first gas source in fluid communication with the first fluid reservoir;
a second gas source in fluid communication with the second fluid reservoir; and
an electronic processor connected to the first and second gas sources,
wherein during operation of the system, the electronic processor is configured to:
initiate injection of a fluid sample from the first fluid reservoir into the first channel by applying a first gas pressure to the first fluid reservoir, thereby causing at least a portion of the fluid sample to enter the first channel; and
terminate injection of the fluid sample by applying a second gas pressure to the second fluid reservoir, thereby causing background fluid to flow from the second fluid reservoir to flow in a uniform direction within the first channel; and
wherein no electrical potential is applied across the fluid sample to inject the sample into the first channel.

22. The system of claim 21, further comprising:
at least two electrodes in communication with the electronic processor,
wherein during operation of the system, the electronic processor is configured to apply an electrical potential difference across the fluid sample in the first channel through the at least two electrodes to electrophoretically separate components of the fluid sample in the first channel.

23. The system of claim 22, further comprising:
a mass spectrometry detector in fluid communication with an output port of the first channel,
wherein during operation of the system, the separated components of the fluid sample are discharged through the output port and into the mass spectrometry detector.

24. The system of claim 21, wherein the second pressure is larger than the first pressure when injection of the fluid sample is terminated.

25. The system of claim 21, wherein the electronic processor is configured to terminate application of the first pressure to the first fluid reservoir when the second pressure is applied to the second fluid reservoir by venting the first fluid reservoir.

26. The system of claim 21, wherein the electronic processor is configured so that:
during a first portion of an injection period for the fluid sample, the electronic processor applies the first pressure to the first fluid reservoir; and
during a second portion of the injection period, the electronic processor applies the second pressure to the second fluid reservoir and applies a third pressure to the first fluid reservoir,
wherein the third pressure is less than the second pressure.

27. The system of claim 26, wherein the electronic processor is configured so that during the first portion of the injection period, the electronic processor applies a fourth pressure to the second fluid reservoir.

28. The system of claim 27, wherein the second pressure is at least 10% less than the fourth pressure.

* * * * *

UNITED STATES PATENT AND TRADEMARK OFFICE
CERTIFICATE OF CORRECTION

PATENT NO. : 10,393,698 B2
APPLICATION NO. : 15/439199
DATED : August 27, 2019
INVENTOR(S) : Mellors et al.

Page 1 of 1

It is certified that error appears in the above-identified patent and that said Letters Patent is hereby corrected as shown below:

In the Specification

Column 4, Line 40: Please correct "EU" to read -- EO --

Signed and Sealed this
Tenth Day of December, 2019

Andrei Iancu
*Director of the United States Patent and Trademark Office*